US008182842B1

(12) United States Patent
Richmond et al.

(10) Patent No.: US 8,182,842 B1
(45) Date of Patent: May 22, 2012

(54) PHYSICO-CHEMICAL-MANAGED KILLING OF PENICILLIN-RESISTANT STATIC AND GROWING GRAM-POSITIVE AND GRAM-NEGATIVE VEGETATIVE BACTERIA

(75) Inventors: Robert Chaffee Richmond, Huntsville, AL (US); Harry F. Schramm, Jr., Winchester, TN (US); Francis G. Defalco, Houston, TX (US); Alex F. Farris, III, Birmingham, AL (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 71 days.

(21) Appl. No.: 12/943,744

(22) Filed: Nov. 10, 2010

(51) Int. Cl.

| | |
|---|---|
| ***A01N 59/26*** | (2006.01) |
| *A61K 33/42* | (2006.01) |
| *A61K 33/00* | (2006.01) |
| *A61K 33/02* | (2006.01) |
| *A01N 59/00* | (2006.01) |

(52) U.S. Cl. ........................ 424/601; 424/600; 424/719

(58) Field of Classification Search .................. 424/601
See application file for complete search history.

(56) References Cited

U.S. PATENT DOCUMENTS

| | | | |
|---|---|---|---|
| 3,792,047 | A | 2/1974 | Arkley et al. |
| 3,890,311 | A | 6/1975 | Wei et al. |
| 5,783,561 | A | 7/1998 | Horwitz et al. |
| 5,866,539 | A | 2/1999 | Blackburn et al. |
| 5,976,542 | A | 11/1999 | Weiser et al. |
| 6,027,906 | A | 2/2000 | Balganesh et al. |
| 6,054,431 | A | 4/2000 | Horwitz et al. |
| 6,288,214 | B1 | 9/2001 | Hook et al. |
| 6,936,252 | B2 | 8/2005 | Gilbert et al. |
| 7,569,223 | B2 | 8/2009 | Fischetti et al. |
| 7,576,054 | B2 | 8/2009 | Walsh et al. |
| 7,713,534 | B2 | 5/2010 | Gilbert et al. |
| 2004/0147441 | A1 | 7/2004 | Leach et al. |
| 2004/0265933 | A1 | 12/2004 | Le Page et al. |

FOREIGN PATENT DOCUMENTS

| | | | |
|---|---|---|---|
| CN | 101584694 | A | 11/2009 |
| JP | 54012376 | A | 1/1979 |
| WO | 2004081036 | A1 | 9/2004 |
| WO | 2007037518 | A1 | 4/2007 |
| WO | 2008117796 | A1 | 2/2008 |

OTHER PUBLICATIONS

Kempe, H.; Kempe, M. Anal. Bioanal. Chem. (2010), 396, 1599-1606 (available online Dec. 12, 2009).*

Lo Nostro, P., et al. Biophysical Chemistry, 2006, v. 124, pp. 208-213 (Available online Apr. 26, 2006).*

Joann Hoskins et al., Penicillin Binding Protein From *Streptococcus pneumoniae*, United States Statutory Invention Registration, May 7, 2002, H2021H, US Patent and Trademark Office.

* cited by examiner

*Primary Examiner* — Johann Richter
*Assistant Examiner* — Erin Hirt
(74) *Attorney, Agent, or Firm* — Absolute Technology Law Group, LLC; James J. McGroary

(57) ABSTRACT

Systems and methods for the use of compounds from the Hofmeister series coupled with specific pH and temperature to provide rapid physico-chemical-managed killing of penicillin-resistant static and growing Gram-positive and Gram-negative vegetative bacteria. The systems and methods represent the more general physico-chemical enhancement of susceptibility for a wide range of pathological macromolecular targets to clinical management by establishing the reactivity of those targets to topically applied drugs or anti-toxins.

36 Claims, 21 Drawing Sheets

PHYSICO-CHEMICAL-MANAGED KILLING OF PENICILLIN-RESISTANT STATIC AND GROWING GRAM-POSITIVE AND GRAM-NEGATIVE VEGETATIVE BACTERIA

STATEMENT REGARDING FEDERALLY SPONSORED RESEARCH OR DEVELOPMENT

The invention described herein was made in part by an employee of the United States Government and may be manufactured and used by and for the Government of the United States for governmental purposes without the payment of any royalties thereon of therefor.

FIELD OF INVENTION

The present invention relates to the field of pharmaceutical compounds and more particularly to physico-chemical alteration of macromolecular targets and target-accessibility to a drug or antitoxin resulting from inclusion of components of the Hofmeister series.

GLOSSARY

Figure 1:
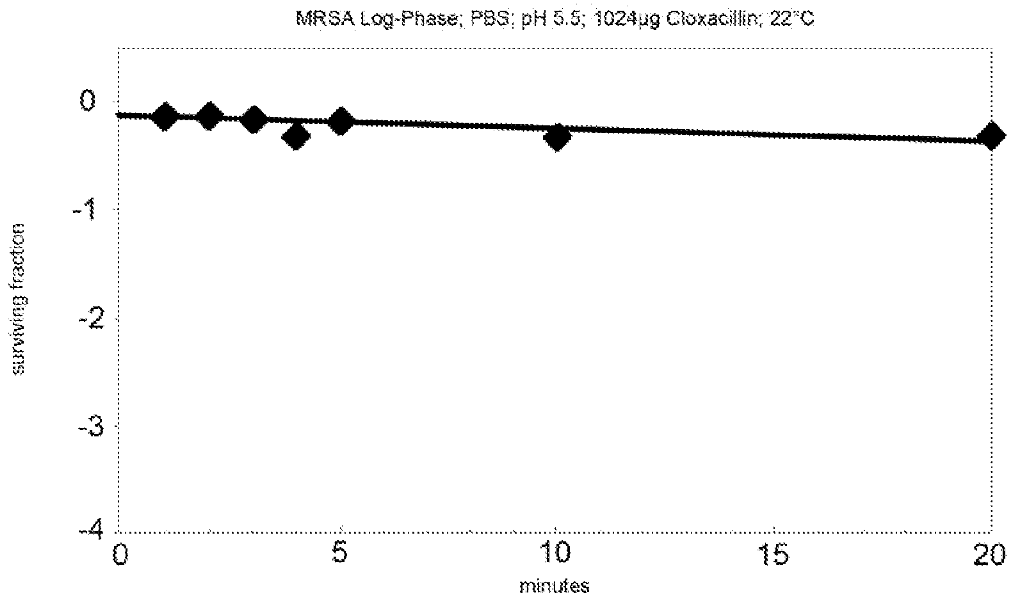
FIG. 1 illustrates the non-substantial killing effect of a pH 5.5 PBS solution having 1024 μg/ml cloxacillin at 22° C. on a logarithmic-phase methicillin-resistant *Staphylococcus aureus* (MRSA) culture over a 20 minute period.
Figure 2:
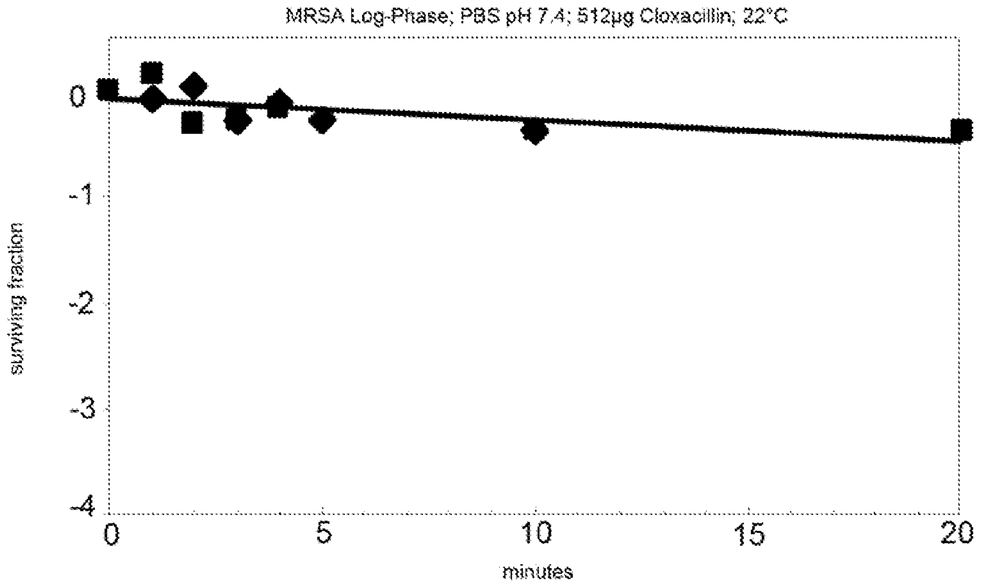
FIG. 2 illustrates the non-substantial killing effect of a pH 7.4 PBS solution having 512 μg/ml cloxacillin at 22° C. on a logarithmic-phase MRSA culture over a 20 minute period.
Figure 3:
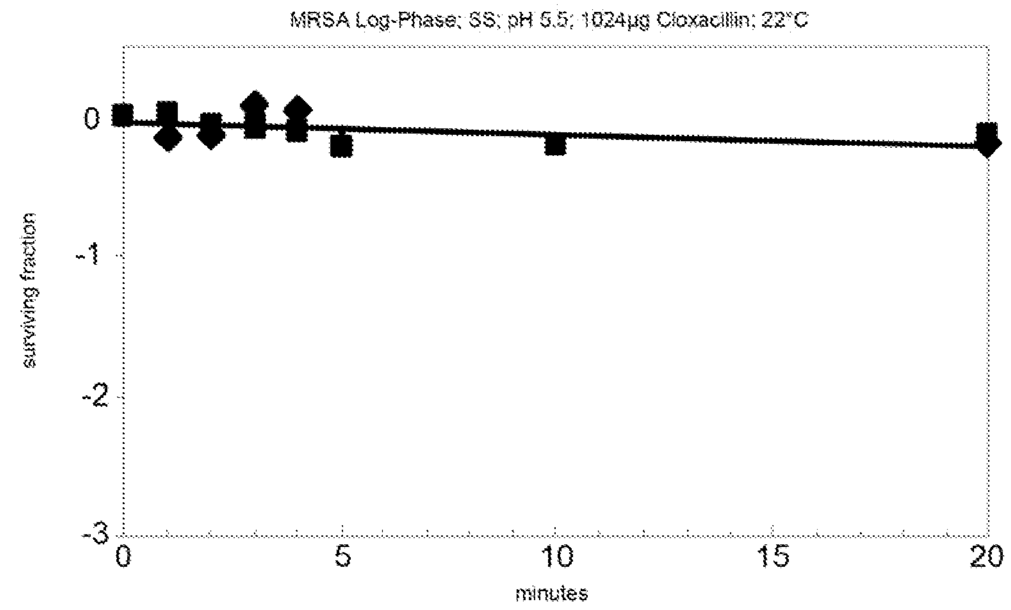
FIG. 3 illustrates the non-substantial killing effect of a pH 5.5 SS having 1024 μg/ml cloxacillin at 22° C. on a logarithmic-phase MRSA culture over a 20 minute period.
Figure 4:
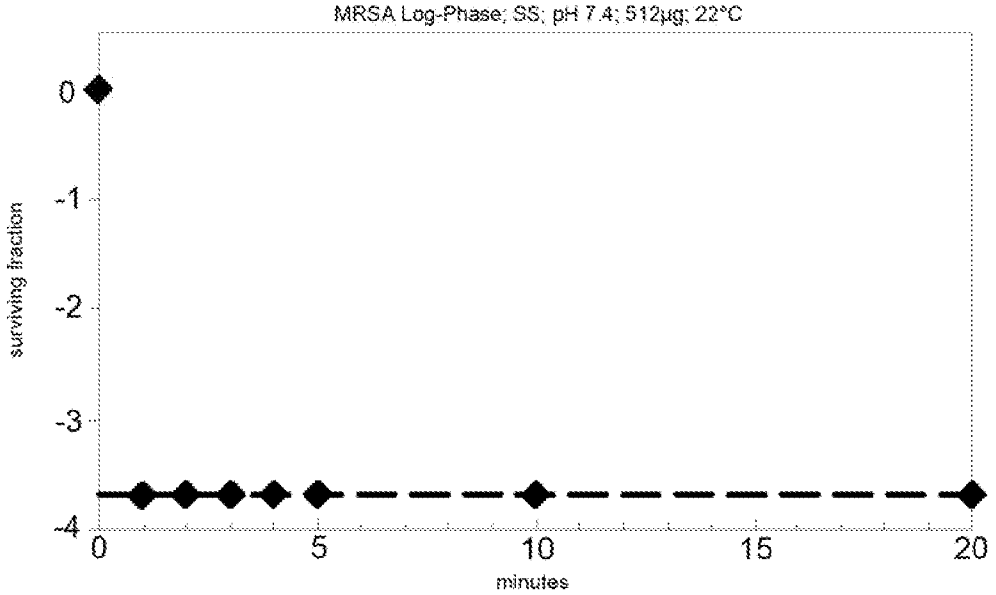
FIG. 4 illustrates the killing effect of a pH 7.4 SS having 512 μg/ml cloxacillin at 22° C. on a logarithmic-phase MRSA culture over a 60 minute period.
Figure 5:
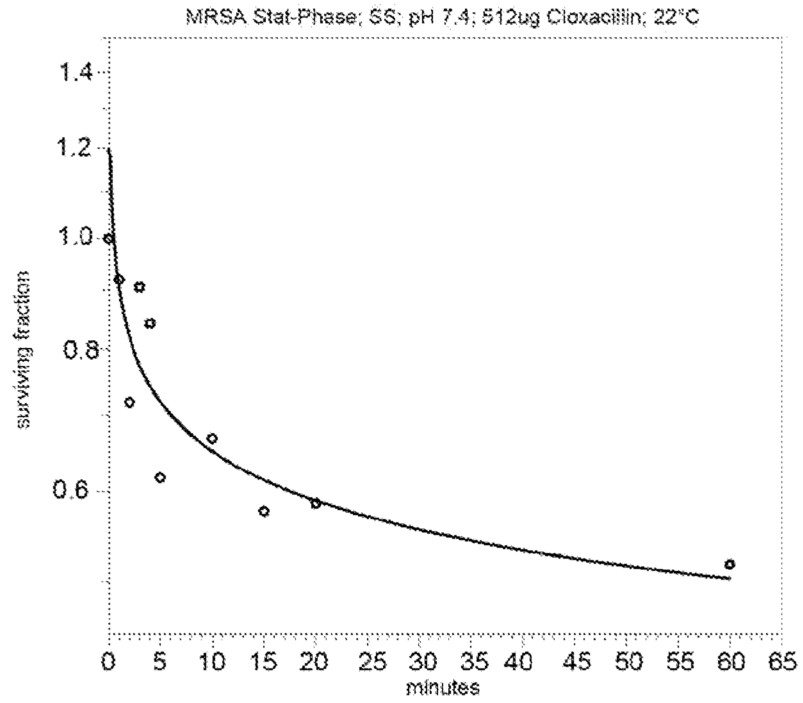
FIG. 5 illustrates the killing effect of a pH 7.4 SS having 512 μg/ml cloxacillin at 22° C. on a stationary-phase MRSA culture over a 60 minute period.
Figure 6:
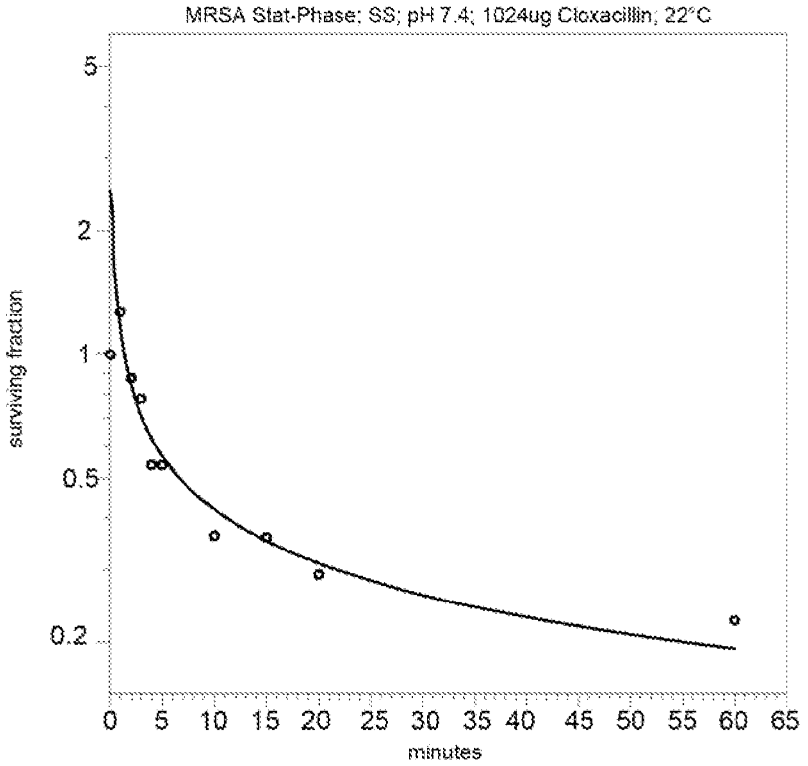
FIG. 6 illustrates the killing effect of a pH 7.4 SS having 1024 μg/ml cloxacillin at 22° C. on a stationary-phase MRSA culture over a 60 minute period.
Figure 7:
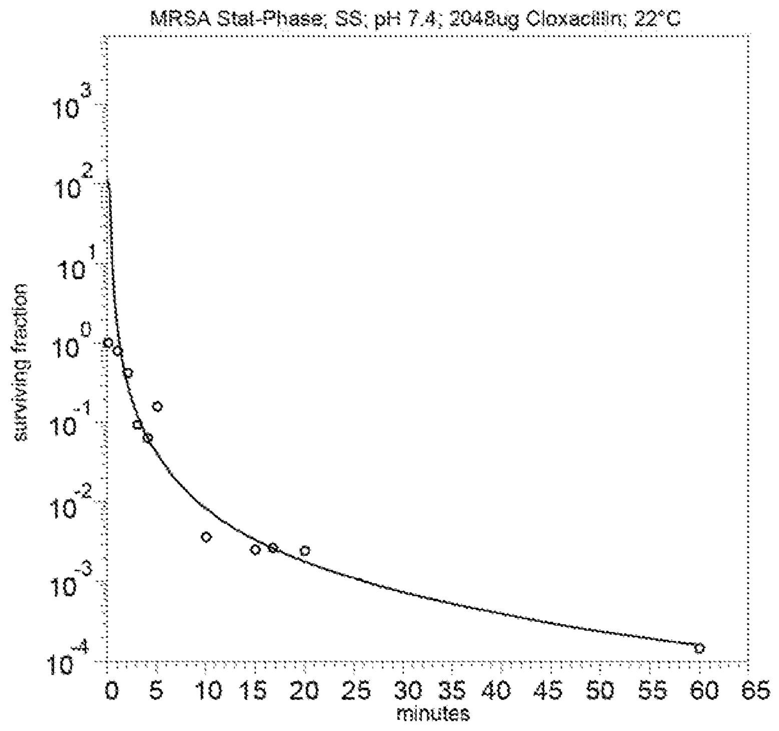
FIG. 7 illustrates the killing effect of a pH 7.4 SS having 2048 μg/ml cloxacillin at 22° C. on a stationary-phase MRSA culture over a 60 minute period.
Figure 8:
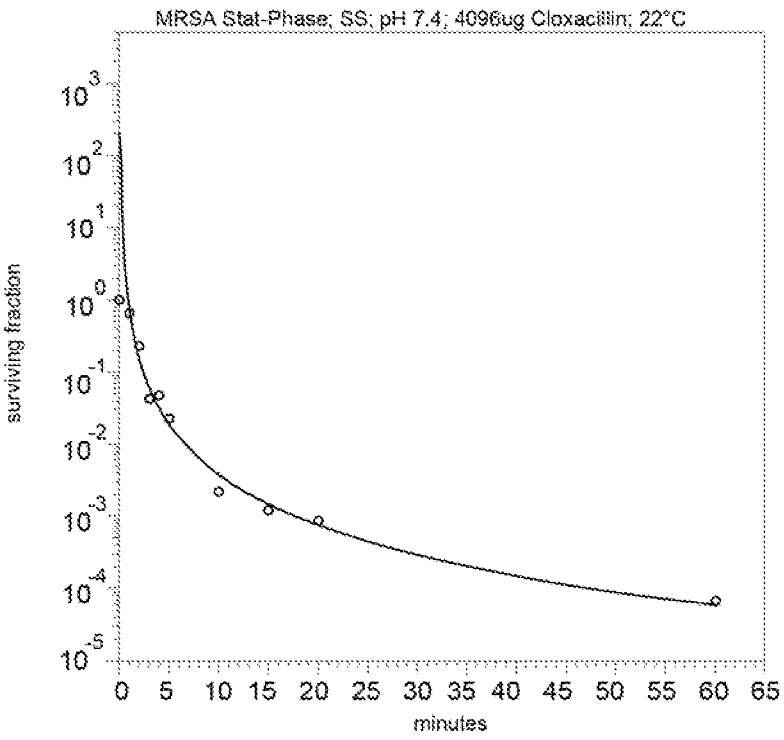
FIG. 8 illustrates the killing effect of a pH 7.4 SS having 4096 μg/ml cloxacillin at 22° C. on a stationary-phase MRSA over a 60 minute period.
Figure 9:
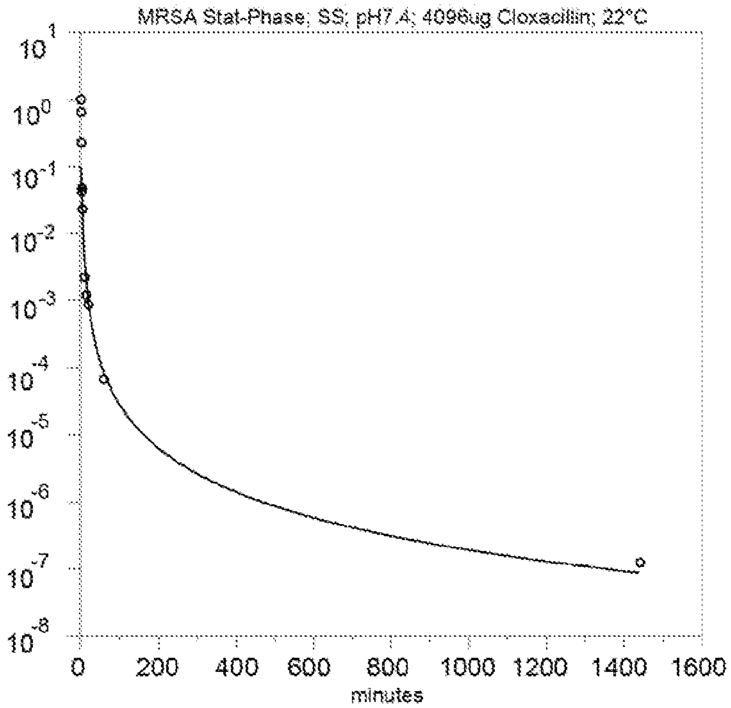
FIG. 9 illustrates the killing effect of a pH 7.4 SS having 4096 μg/ml cloxacillin at 22° C. on a stationary-phase MRSA culture over a 24 hour period.
Figure 10:
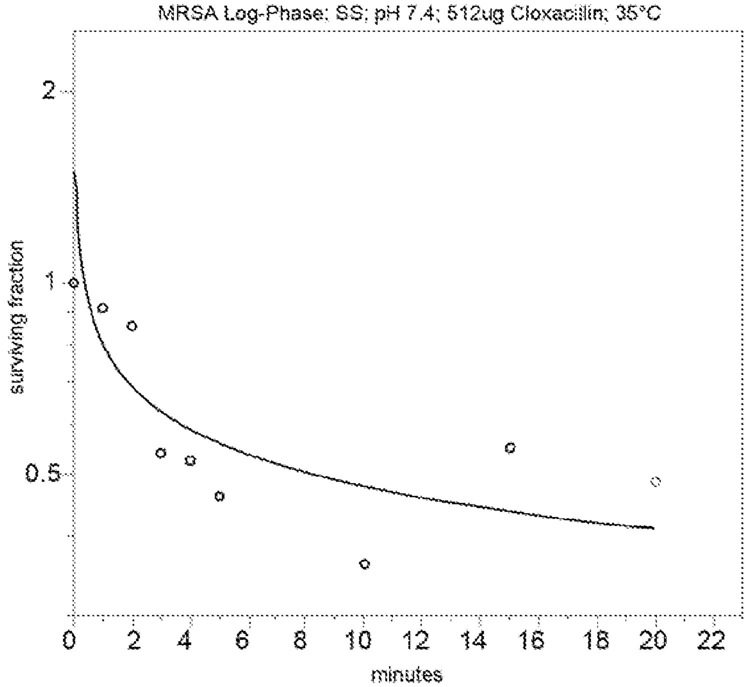
FIG. 10 illustrates the killing effect of a pH 7.4 SS having 512 μg/ml cloxacillin at 35° C. on a logarithmic-phase MRSA culture over a 20 minute period.
Figure 11:
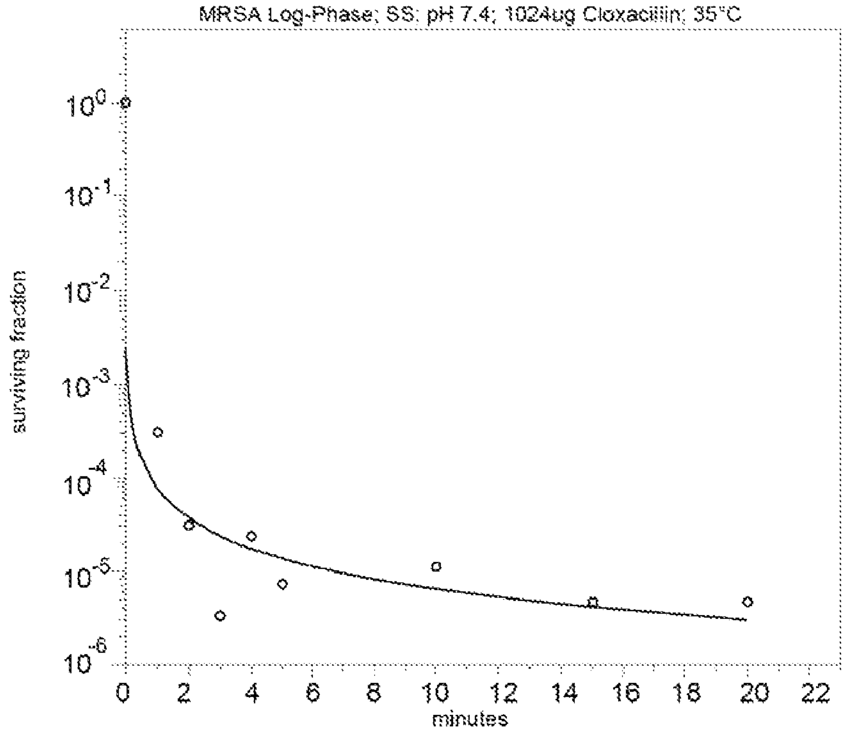
FIG. 11 illustrates the killing effect of a pH 7.4 SS having 1024 μg/ml cloxacillin at 35° C. on a logarithmic-phase MRSA culture over a 20 minute period.
Figure 12:
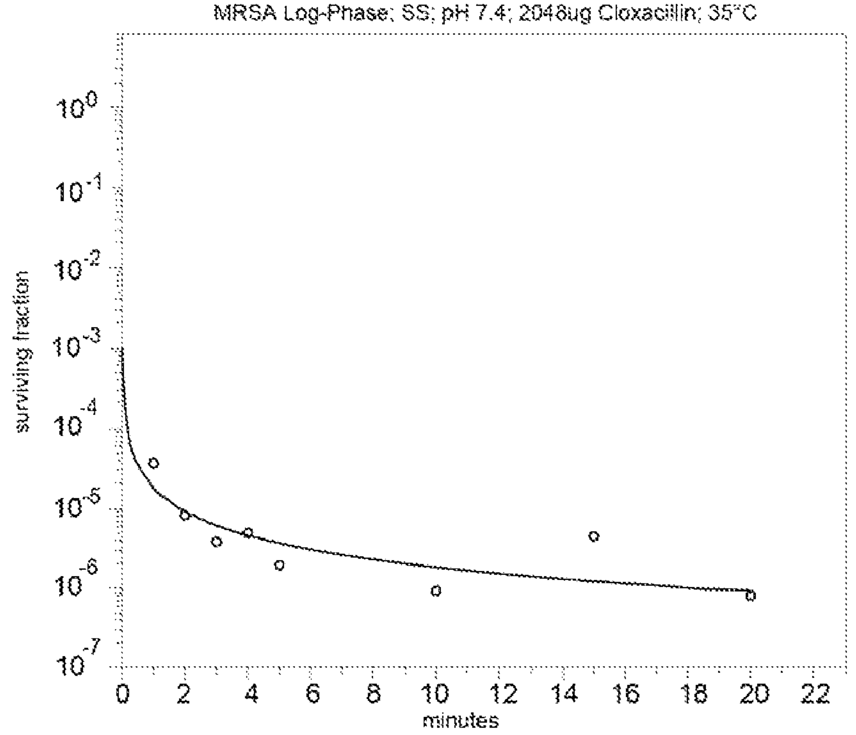
FIG. 12 illustrates the killing effect of a pH 7.4 SS having 2048 μg/ml cloxacillin at 35° C. on a logarithmic-phase MRSA culture over a 20 minute period.
Figure 13:
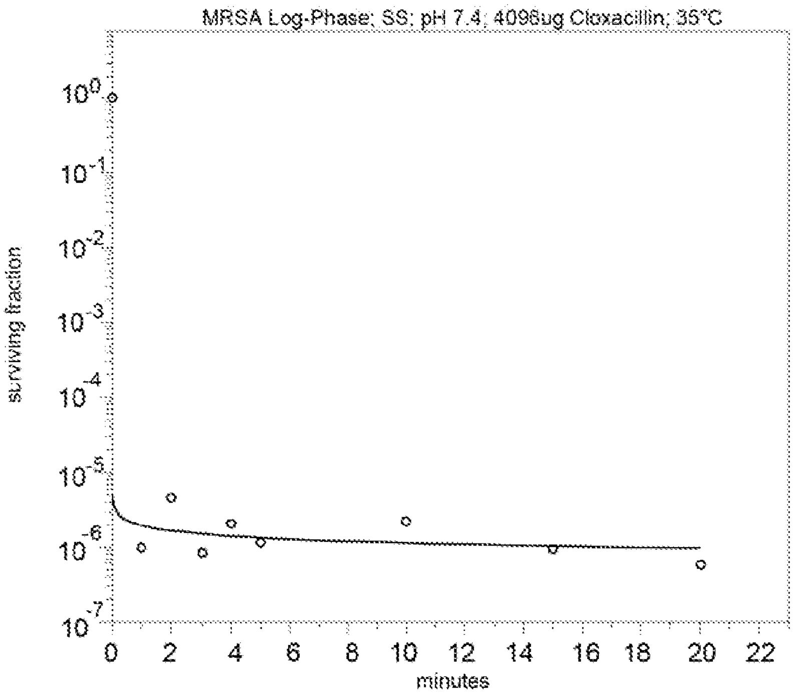
FIG. 13 illustrates the killing effect of a pH 7.4 SS having 4096 μg/ml cloxacillin at 35° C. on a logarithmic-phase MRSA culture over a 20 minute period.
Figure 14:
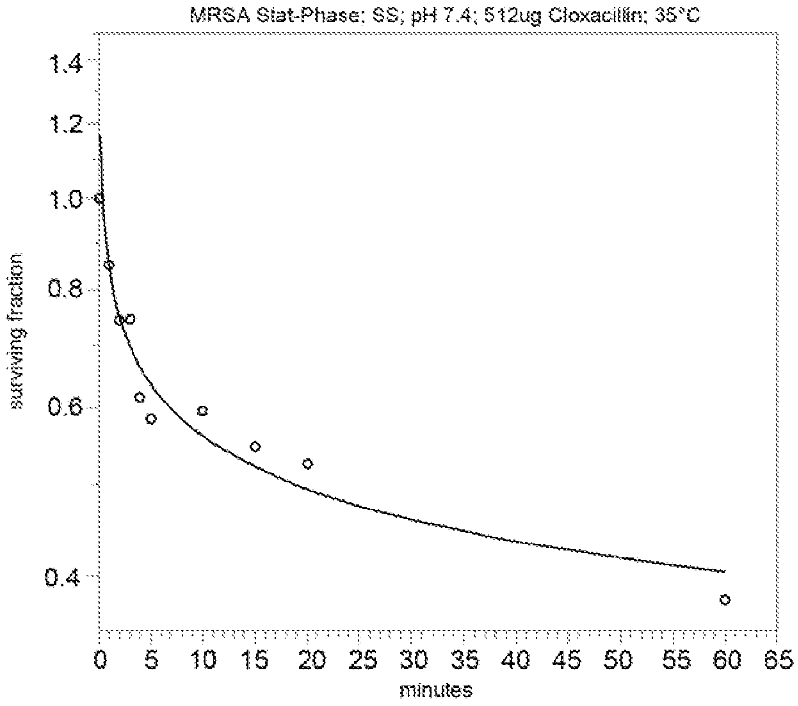
FIG. 14 illustrates the killing effect of a pH 7.4 SS having 512 μg/ml cloxacillin at 35° C. on a stationary-phase MRSA culture over a 60 minute period.
Figure 15:
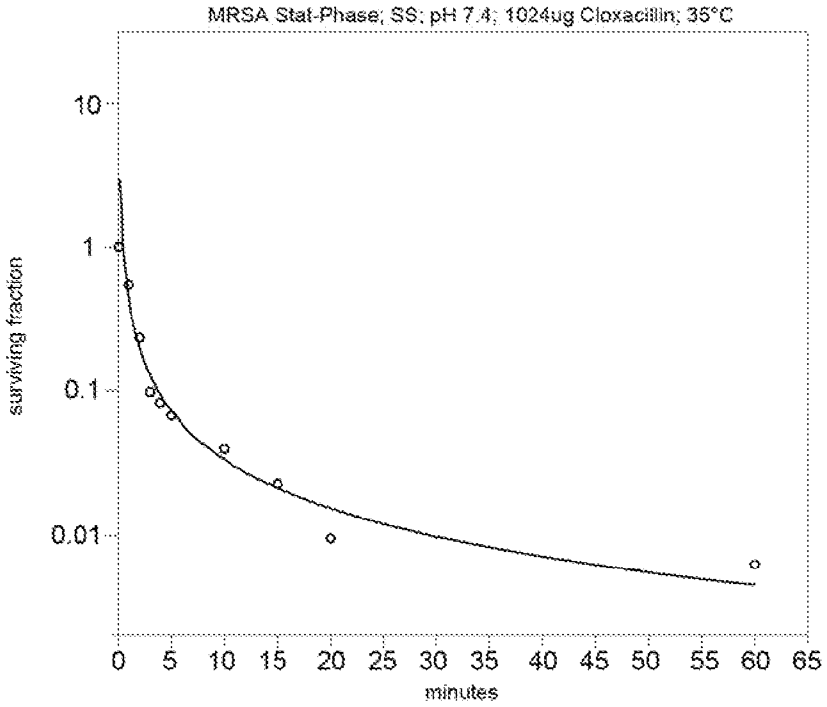
FIG. 15 illustrates the killing effect of a pH 7.4 SS having 1024 μg/ml cloxacillin at 35° C. on a stationary-phase MRSA culture over a 60 minute period.
Figure 16:
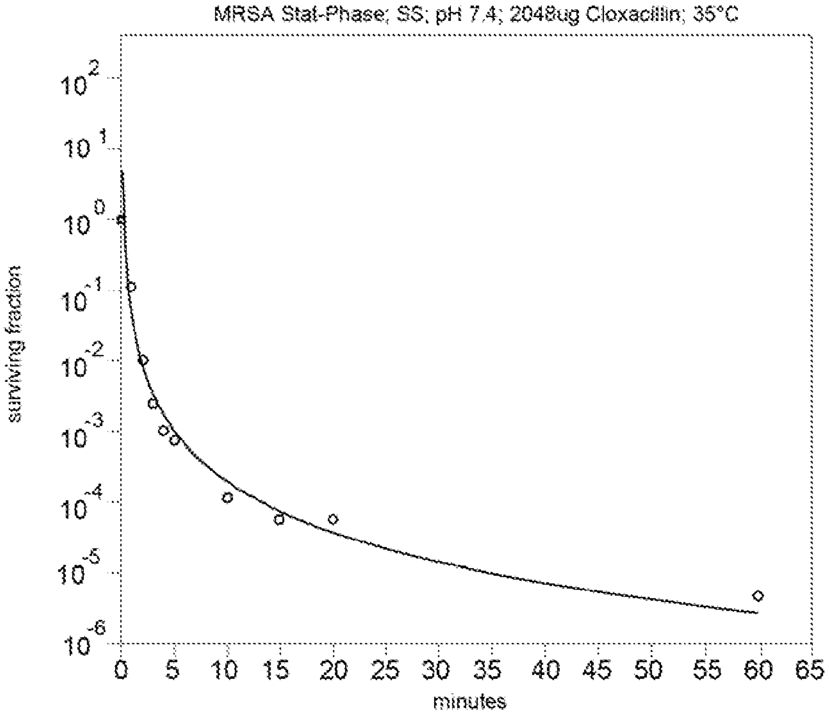
FIG. 16 illustrates the killing effect of a pH 7.4 SS having 2048 μg/ml cloxacillin at 35° C. on a stationary-phase MRSA culture over a 60 minute period.
Figure 17:
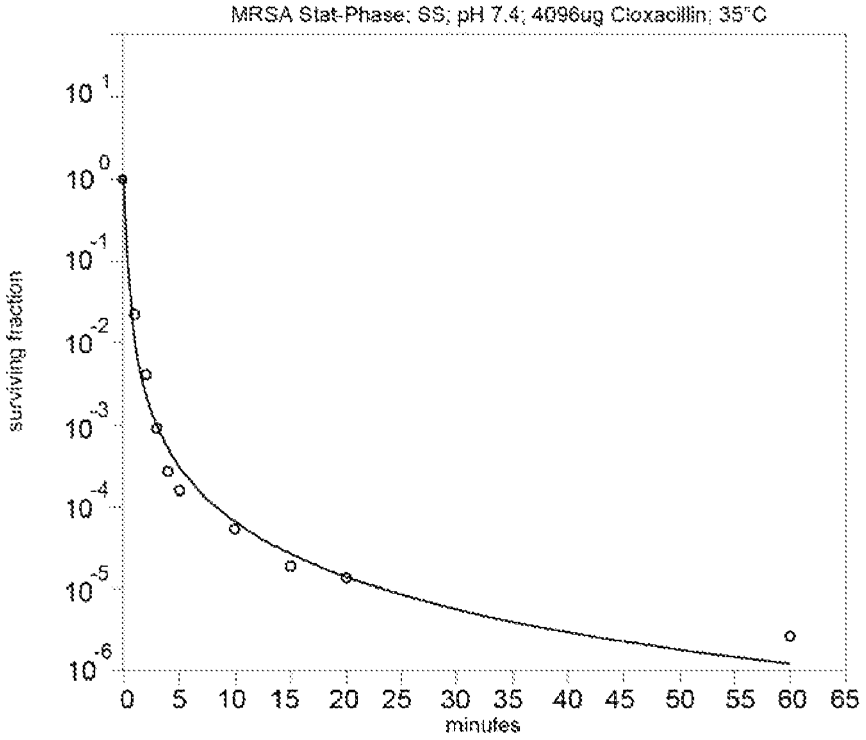
FIG. 17 illustrates the killing effect of a pH 7.4 SS having 4096 μg/ml cloxacillin at 35° C. on a stationary-phase MRSA culture over a 60 minute period.
Figure 18:
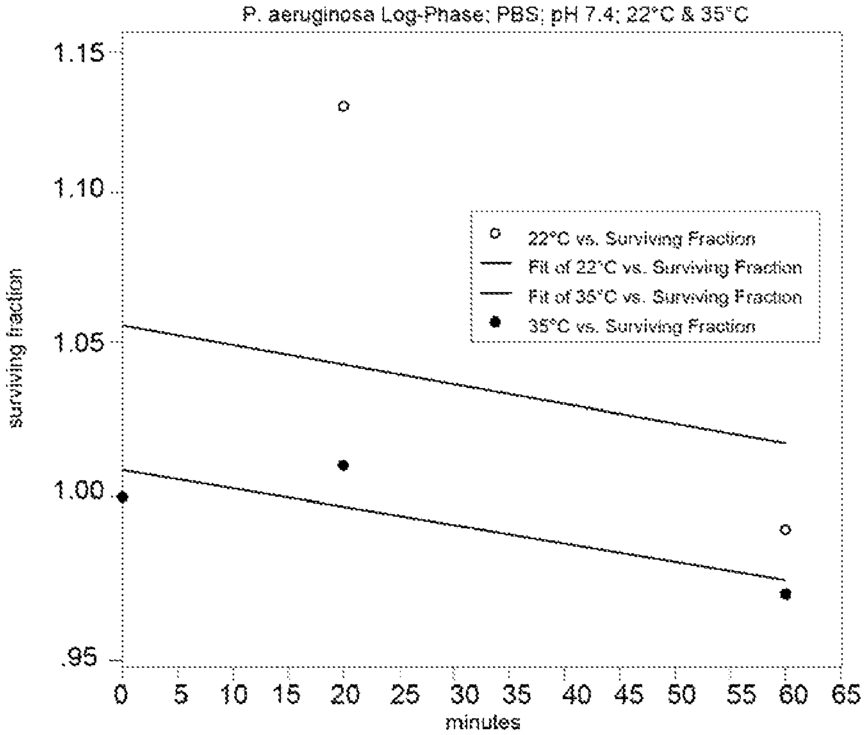
FIG. 18 illustrates the non-substantial killing effect of a pH 7.4 PBS solution at 22° C. and 35° C. on a logarithmic-phase *Pseudomonas aeruginosa* culture over a 60 minute period.
Figure 19:
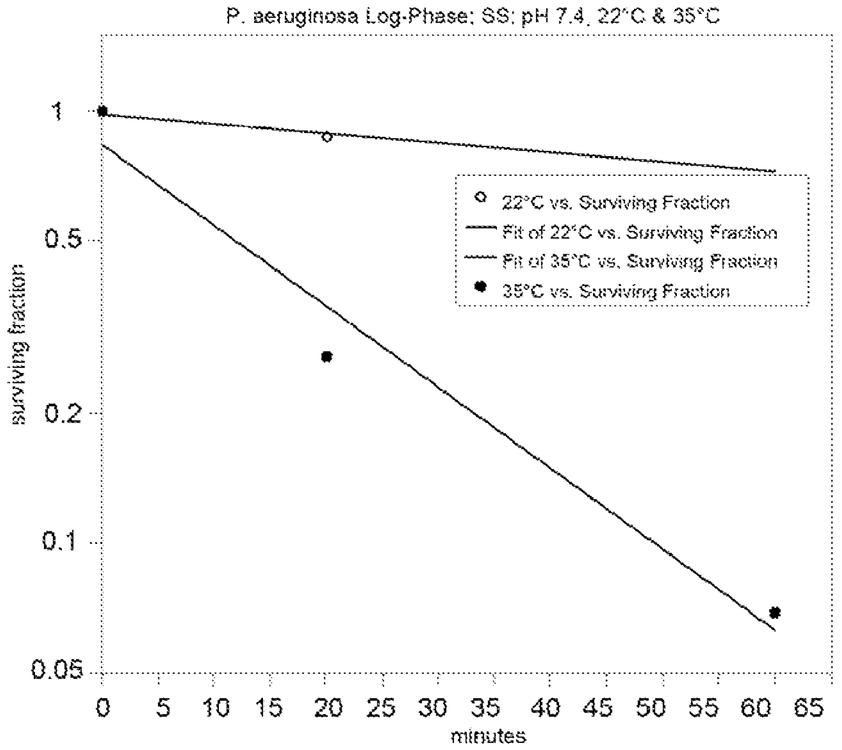
FIG. 19 illustrates the non-substantial killing effect of a pH 7.4 SS at 22° C. and 35° C. on a logarithmic-phase *Pseudomonas aeruginosa* culture over a 60 minute period.
Figure 20:
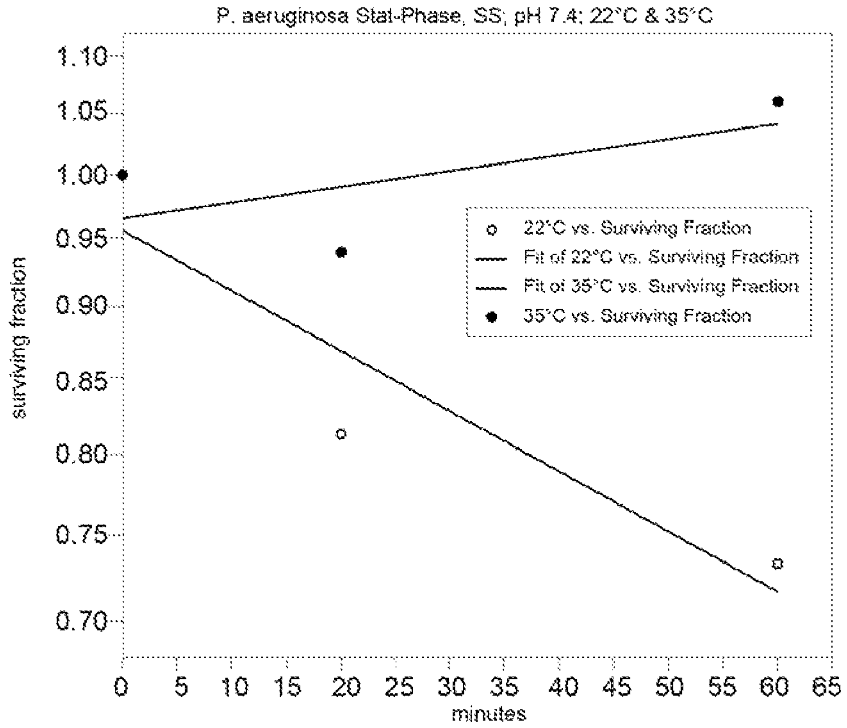
FIG. 20 illustrates the non-substantial killing effect of a pH 7.4 PBS solution at 22° C. and 35° C. on a stationary-phase *Pseudomonas aeruginosa* culture over a 60 minute period.

As used herein, the term "humectant" refers to a substance that absorbs water, helps another substance retain moisture, and/or disrupts or affects the water activity of macromolecules. Humectants include compounds in the Hofmeister series, including, but not limited to chaotropes, kosmotropes, and astringents or styptics, such as alum, Burow's solution (i.e., aluminum acetate), and silver nitrate, which at concentrations of approximately 10 mM or less also acts as an anti-toxin and antiseptic.

As used herein, the term "penicillin" refers to any of a group of broad-spectrum antibiotic drugs of the central formula R—$C_9H_{11}N_2O_4S$, obtained from penicillin molds or produced synthetically, and which are most active against Gram-positive bacteria principally due to a beta-lactam ring reacting with a -serine-X-X-lysine-amino acid motif in the bacteria's transpeptidases, where X is any amino acid. Penicillins are used in the treatment of various bacterial infections and diseases. Penicillins include, but are not limited to, methicillin, cloxacillin, amoxicillin, ampicillin, carbenicillin, dicloxacillin, oxacillin, and therapeutic equivalents.

As used herein, the term "salt" refers to a chemical compound derived from an acid by replacing a hydrogen, wholly or partly, with a metal or an electropositive radical. This includes ionic products of Brønsted-Lowry acid-base reactions and ionic products of Lewis acids in water, i.e., conjugate bases, where both these forms of salts are found within the Hofmeister series.

As used herein, "SS" is an abbreviation for a salt solution for denaturing, i.e., altering the structure of, macromolecules, and which is comprised of compounds within the Hofmeister series.

As used herein, "PBS" is an abbreviation for non-denaturing phosphate buffered saline, a buffer solution commonly used to suspend and wash cells.

BACKGROUND

Both Gram-positive and Gram-negative pathogenic bacteria are causing significant health problems around the world due to these bacteria developing, or innately presenting, biochemical mechanisms that thwart medical management by various types of antibiotics. Effective use of pencillins, one major class of antibiotics, is particularly being threatened. For examples, Gram-positive methicillin-resistant *Staphylococcus aureus* (MRSA) has become resistant to control by penicillins, and *Pseudomonas aeruginosa*, an opportunistic member of Gram-negative bacteria, is innately beyond control of penicillins.

One area of concern is hospital-acquired or nosocomial parenteral antibiotic-resistant bacterial infections from topical colonized bacteria or suppurating infections. These types of bacteria frequently escape sterilization efforts prior to invasive procedures allowing them to enter the body and establish infection.

The acquiring of penicillin resistance by bacteria is life-threatening and is being addressed by the pharmaceutical industry through the development of new generations of penicillins. The pharmaceutical industry largely directs its efforts to creating new molecular alterations of existing penicillins in order to circumvent continually evolving resistance that in turn defeats efficacy of such new penicillins. Each generation of penicillins successively targets penicillin-resistant mechanisms in the bacterial coat in a way designed to circumvent biochemical resistance mechanisms that have evolved within pathogenic bacteria to resist previous generations of penicillins. It is unlikely that this cycle of new biochemical specificity for penicillin activity, followed by evolving resistance to that specificity, will be therapeutically successful since the percentages of penicillin-resistant pathogenic variants that defeat antibiotic management is rapidly increasing.

Penicillins bind to penicillin-binding proteins (PBPs) in the bacterial coat, and especially in Gram-positive bacteria those targets tend to evolve into non-binding or non-accessible motifs where, for example, one binding motif is said to be a 4-amino acid sequence -serine-X-X-lysine- that provides covalent acylation of serine by the beta-lactam ring of penicillins. In Gram-negative bacteria, resistance to penicillins is additionally complicated by the presence of transporters in the coat-associated outer membrane that export the influx of penicillin, and by similarly located porins that can restrict uptake of penicillin. Therefore, it is important to resolve both the evolved resistance to binding of penicillin to amino acid target motifs and the blockage of uptake of penicillin into cells, which together largely account for observed antibiotic resistance.

It is known that covalent binding of penicillins to PBPs of actively replicating bacterial cells leads to defective coats, which ultimately cause cell lysis and death. It is known that this covalent binding is commonly defeated by evolution of structural alteration in PBPs during development of penicillin resistance.

In addition, penicillin transport mechanisms also require proteins of specific structure to perform the function of penicillin efflux. Structural alterations of these proteins by pH, salt concentration, or dehydration are often reversible. For example, for at least one strain of MRSA, penicillin resistance is observed at pH 7.4; however, penicillin sensitivity is returned when those bacteria are exposed to penicillin at pH 5.6. Conversely to physico-chemically induced reversible denaturation, covalent binding of penicillin to PBP targets is not reversible, but rather immutable whether achieved in growing or static bacterial cells.

It is desirable to have a system and method for killing topical bacteria known to be penicillin-resistant, particularly MRSA and *Pseudomonas aeruginosa*.

It is desirable to have a system and method for reversing the levels of penicillin-resistant bacterial infections that plague individuals in both community and hospital settings.

It is desirable to have a system and method for managing penicillin-resistance by mechanisms other than biochemical advances in the structure and/or activity of penicillin.

It is further desirable to have a system and method for altering in situ targets and inaccessibility of penicillin in bacteria by physico-chemical treatments, providing novel paradigms for effective topical applications of antibiotics and other drugs and antitoxins.

SUMMARY OF THE INVENTION

The present invention is embodied as a pharmaceutical solution at pH 7.4 comprised of high concentrations of phosphate, sulfate, and acetate anions, potassium and ammonium cations, a trace of free ammonia, penicillin, and water. In an exemplary embodiment, the SS is applied within a range of temperatures, specifically 22° C. and 35° C. The SS is capable of inducing alteration of bacterial in situ target proteins to create sensitivity of the bacteria to otherwise ineffective penicillins.

DETAILED DESCRIPTION OF INVENTION

For the purpose of promoting an understanding of the present invention, references are made in the text to exemplary embodiments of a system and method for the physico-chemical alteration of penicillin-binding proteins in penicillin-resistant Gram-positive and Gram-negative bacteria to induce sensitivity to otherwise ineffective penicillins, only one of which is described herein. It should be understood that no limitations on the scope of the invention are intended by describing these exemplary embodiments. One of ordinary skill in the art will readily appreciate that alternate but functionally equivalent use of compounds, solvents, concentrations, pH, and methods may be used to expand biochemical target reactivity and accessibility to reactive drugs and anti-toxins. The inclusion of additional elements, such as drugs and anti-toxins, depending upon the specific biochemical targets and conditions involved, may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

Moreover, the terms “substantially” or “approximately” as used herein may be applied to modify any quantitative representation that could permissibly vary without resulting in a change in the basic function to which it is related.

The physico-chemical aspect of the SS, less penicillin, is conceived upon knowledge of water activity relative to biological macromolecular rearrangements, and the knowledge that temperature and pH also affect these rearrangements. The specifics of the SS, less penicillin, are taken from the extensive Hofmeister series for enhancing reversible denaturation of macromolecules in Gram-positive bacteria (e.g., methicillin-resistant *Staphylococcus aureus*) and Gram-negative bacteria (e.g., *Pseudomonas aeruginosa*). The Hofmeister series is comprised of compounds known to effect water activity and stability of a substantial and varied range of macromolecules. The physico-chemical conditions of reversible denaturation rearrange biological macromolecules, thereby altering target motifs in protein, inhibiting structure-specific protein activities, altering passive diffusion through structural barriers, and imposing a temporal static state upon many metabolic processes, thereby improving outcome from coincident therapeutic treatment of targets. That is, such a disrupted and static condition in bacteria can be used as an advantage by including one or more different drugs or anti-toxins in this denaturing solution; drugs and anti-toxins can include a range of known biochemical agents, such as penicillin, antiseptics, or disinfectants selected for compatibility with normal tissue at the site of topical application. In this embodiment, cloxacillin, an otherwise substantially ineffective penicillin, was chosen and proved to be highly efficient in directly killing bacteria normally resistant to penicillin.

FIGS. 1 through 41 illustrate the efficiency of a SS formulation derived from members of the Hofmeister series for physico-chemically inducing alteration of in situ target proteins to establish sensitivity of Gram-positive (i.e., MRSA) and Gram-negative bacteria (i.e., *Pseudomonas aeruginosa*) to otherwise ineffective penicillins.

The SS formulation at pH 7.4, but not pH 5.5, is effective in reversing penicillin-resistance in a methicillin-resistant strain of *Staphylococcus aureus* (MRSA) and in *Pseudomonas aeruginosa*, important bacterial pathogens. The SS affects water activity, which in turn alters the macromolecular structure of the target. In this manner, penicillin-resistant proteins are rearranged by physico-chemical conditions such that covalent binding of penicillins is allowed and the structures of penicillin transport proteins are altered or thereby inactivated to defeat the function of penicillin efflux.

In an exemplary embodiment for treatment of planktonic bacteria, the SS contains high, at times saturated, concentrations of phosphate, sulfate, and acetate anions, potassium and ammonium cations, plus a small concentration of free ammonia, all prepared in water, and applied at 22° C. or 35° C. For example, in one embodiment, the molar concentrations of the phosphate, sulfate, and acetate anions may be 3.1 M, 0.4 M, and 0.2 M, respectively, and the potassium and ammonium cations may be 2.6 M and 3.7 M, respectively. In an exemplary embodiment, ammonium hydroxide is added to the SS in order to bring the SS to the desired pH (e.g., pH 7.4), resulting in a small amount of free ammonia. In various other embodiments, sulfuric acid, acetic acid, a combination thereof, or another acid is added to lower the pH of the SS. In various embodiments, each compound may have a molar concentration ranging from 0.01 M to 4.0 M. In addition, the SS may include any of the compounds in the Hofmeister series; the specific formula of the SS may be adjusted for maximal physico-chemical effectiveness in each specific application.

In various physico-chemical embodiments, the pH, concentrations, solvents and/or temperature of the formulations may vary in order to maximize the effectiveness of macromolecular rearrangements and the outcome for different pathological biomolecular targets, all with regard for the tolerance of the normal tissue involved in topical applications. For example, the temperature may range from freezing to 43° C., the limiting temperature for thermal pain sensation. In various embodiments, the solvent (i.e., water) may be blended with or replaced with a substance(s) that is known to affect water activity and macromolecular rearrangements, such as alcohols (e.g., ethanol, propanol, butanol) or aprotic solvents (e.g., dimethyl acetamide, dimethyl formamide, dimethyl sulfoxide).

In an exemplary embodiment, the SS is prepared to an effective pH of 7.4. In various other embodiments, the SS may be prepared to a pH ranging from 3.5 to 10. The pH may be varied to maximize the effectiveness of the macromolecular rearrangements and the outcome for different pathological biomolecular targets.

In an exemplary embodiment, the SS formulation, often acting as a humectant, is dictated by the alteration of water activity that leads to reversible denaturation of biomolecules, both those that are targets and those affecting accessibility to targets, thereby maximizing the effectiveness of the macromolecular arrangements and the resulting outcome. In various embodiments, the formulation of SS may be varied by the addition of additives that affect the water activity of biomolecules. These additives are taken from the Hofmeister series, and include chaotropes and kosmotropes, including humectants characterized as astringents or styptics, such as alum, Burow's solution (i.e., aluminum acetate), and silver nitrate. These additives are used to effect the reversible denaturation of biomolecules resulting in effective presentation of a variety of new biomolecular targets to drugs or anti-toxins, such as silver nitrate, contained within the topical solutions.

FIGS. 1 through 17 illustrate kill curve time course experiments of stationary and logarithmic-phase MRSA bacterial suspensions exposed to PBS as well as denaturing SS at pH 5.5 or pH 7.4 in the presence of cloxacillin concentrations spanning from 512 μg/ml to 4096 μg/ml. Experiments were conducted at 22° C. or 35° C. The completion time for the experiments ranged from 20 minutes to 24 hours.

For these experiments, the MRSA strain was grown overnight in Mueller-Hinton broth (MH)+2% NaCl at 35° C., subcultured into fresh media, and grown to mid-logarithmic phase. The cells were centrifuged and resuspended in pH 7.4 MH+2% NaCl to produce an $OD_{600}$ nm known to indicate logarithmic-phase or stationary-phase of growth. An appropriate volume of cells was added to 1 ml of buffered SS in a 10 ml Falcon tube to yield a final concentration of ca. $1\times10^8$ colony forming units (CFU)/ml, except for the experiments of FIGS. 1-4 where the final concentration of ca. $1\times10^6$ CFU/ml applies. Survival was determined for bacteria held for varied exposure times of up to 24 hours in the SS or in PBS at pH 5.6 or pH 7.4, each altered with cloxacillin concentrations ranging in doublings from 512 μg/ml to 4096 μg/ml. Survival was measured from samples held at 22° C. and 35° C. After exposure, samples of 50 μl were then withdrawn and a serial dilution series established. Cells were then plated on MH+2% NaCl agar plates and incubated at 22° C. or 35° C. for CFU formation, after which colonies were counted, surviving fractions recorded, and survival curves constructed. Triplicate experiments were conducted for each exposure condition. The cells were treated under static conditions in all cases and treatments were always made on cells held in salt solutions, never on cells held in growth media. In addition to logarithmic-phase cells, stationary-phase cells removed from growth cycle were also treated.

Cells exposed to SS at pH 7.4 in the presence of cloxacillin are killed. Killing is more efficient for logarithmic-phase cells than for stationary-phase cells. Both logarithmic-phase and stationary-phase cells are killed more effectively by treatment at 35° C. than treatment at 22° C.

Killing efficiency is evaluated as therapeutically sufficient according to the $10^{-5}$ level of killing in 5 minutes specified by the British Standard BS EN 1276:1997 Chemical Disinfectants and Antiseptics, which is referred to as the gold standard for efficacy of bactericidal agents. Typically, agents meeting the British Standard are too toxic for human topical application. However, this is not a restriction for effective SS containing cloxacillin used in the illustrated embodiment.

As developed in FIGS. 1 through 4, substantial killing of static logarithmic-phase MRSA by cloxacillin is achieved at pH 7.4 at 22° C. for SS only. PBS at pH 5.5 or at pH 7.4 is not effective, and neither is SS at pH 5.5. Regarding the results shown in FIG. 4, no survivors were seen on any of the treated plates; therefore, the surviving fraction for all time points is less than the $2\times10^{-4}$ indicated as a conservative maximum allowed for the dilution factor plated. Experiments were also conducted on MRSA logarithmic-phase cells with SS alone at 22° C. No killing effect was seen at pH 5.6 or pH 7.4 for SS alone.

As FIGS. 5 through 9 illustrate, the efficiency of killing of stationary-phase MRSA cells at 22° C. does not provide the $10^{-5}$ level of killing in 5 minutes specified by the British Standard. However, at the highest concentration of cloxacillin, that is, 4096 μg/ml, the $10^{-5}$ level of killing is achieved in 3 hours, as detailed in FIG. 9.

As shown in FIGS. 10 through 13, killing is enhanced by exposure of logarithmic-phase MRSA to cloxacillin at 35° C.

As FIGS. 14 through 17 illustrate, the enhanced killing extends to stationary cells exposed at 35° C. as well. The efficiency of killing of both logarithmic-phase and stationary-phase MRSA cells at 35° C. approaches or exceeds the $10^{-5}$ level of killing in 5 minutes specified by the British Standard.

The level of killing is concentration dependent and is based upon the conditions of the treatment, such as species and initial sensitivity/resistance, whether the cells are in a stationary or logarithmic growth phase, temperature, and specific Hofmeister series compounds used.

FIGS. 18 through 41 illustrate kill curve time-course experiments of stationary-phase and logarithmic-phase *Pseudomonas aeruginosa* bacterial suspensions exposed to PBS, to SS, to PBS in the presence of cloxacillin concentrations spanning from 512 μg/ml to 4096 μg/ml, or to SS in the presence of cloxacillin concentrations spanning from 512 μg/ml to 4096 μg/ml. Experiments were conducted at 22° C. or 35° C. over the course of 10, 20, or 60 minutes.

*Pseudomonas aeruginosa* cells were prepared as described above for MRSA with a few exceptions. The *Pseudomonas aeruginosa* cells were first grown in trypticase soy broth and then frozen in aliquots, which were later rescued into MH broth+2% NaCl for use as in the MRSA experiments. An appropriate volume of cells was added to 1 ml of comparative salt solutions in a 10 ml Falcon tube to yield a final concentration of ca. $1\times10^8$ colony forming units (CFU)/ml. Survival was determined for bacteria held for varied exposure times of up to 60 minutes in PBS, in SS, in PBS altered with cloxacillin concentrations ranging in doublings from 512 μg/ml to 4096 μg/ml, or in SS containing cloxacillin concentrations ranging in doublings from 512 μg/ml to 4096 μg/ml. The salt solutions were compared at a pH of 5.6 or 7.4. Survival was measured from samples held at 22° C. or 35° C. After exposure, samples of 50 μl were then withdrawn and a serial dilution series established. Cells were then plated on MH+2% NaCl agar plates and incubated at 22° C. or 35° C. for CFU formation, after which colonies were counted, surviving fractions recorded, and survival curves constructed. Triplicate experiments were conducted for each exposure condition. The cells were treated under static conditions in all cases and treatments were always made on cells held in salt solutions, never on cells held in growth media. In addition to logarithmic-phase cells, stationary-phase cells removed from growth cycle were also treated.

Figure 21:
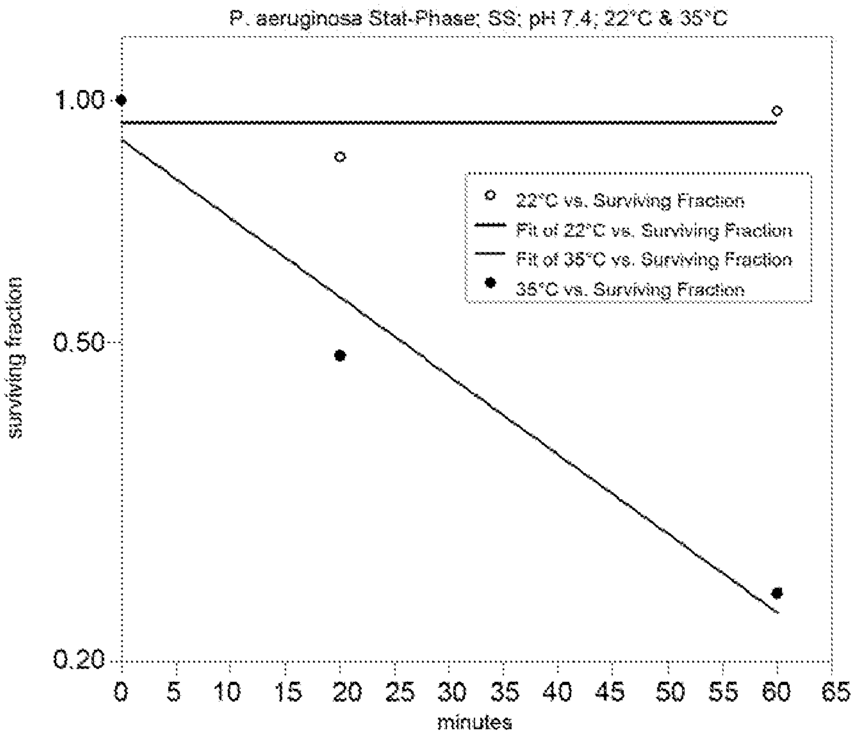
FIG. 21 illustrates the non-substantial killing effect of a pH 7.4 SS at 22° C. and 35° C. on a stationary-phase *Pseudomonas aeruginosa* culture over a 60 minute period.
Figure 22:
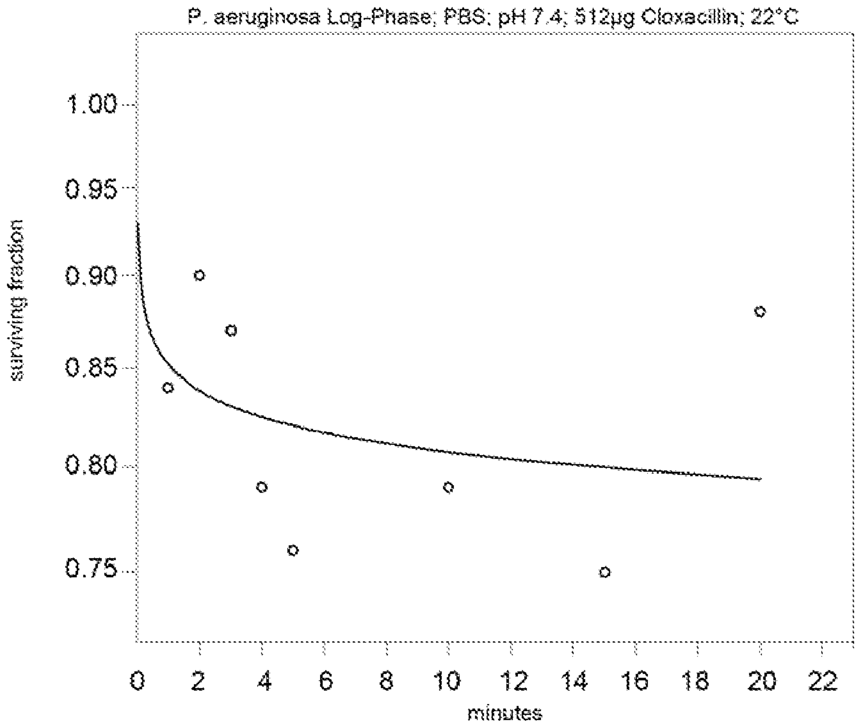
FIG. 22 illustrates the non-substantial killing effect of a pH 7.4 PBS solution having 512 μg/ml cloxacillin at 22° C. on a logarithmic-phase *Pseudomonas aeruginosa* culture over a 20 minute period.
Figure 23:
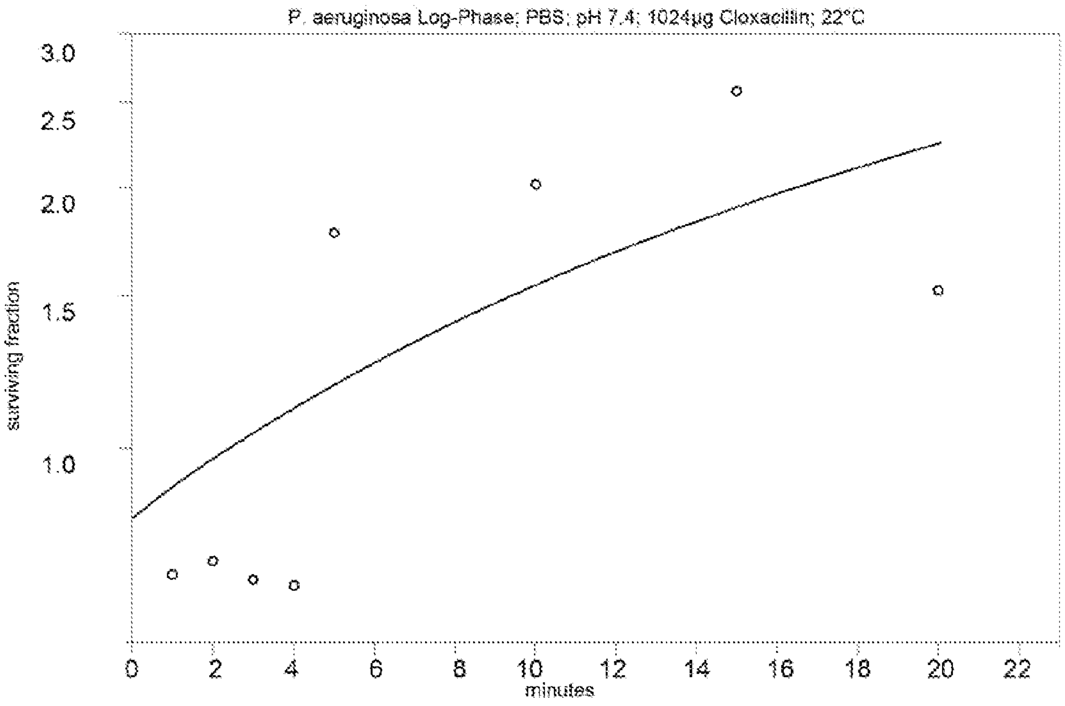
FIG. 23 illustrates the non-substantial killing effect of a pH 7.4 PBS solution having 1024 μg/ml cloxacillin at 22° C. on a logarithmic-phase *Pseudomonas aeruginosa* culture over a 20 minute period.
Figure 24:
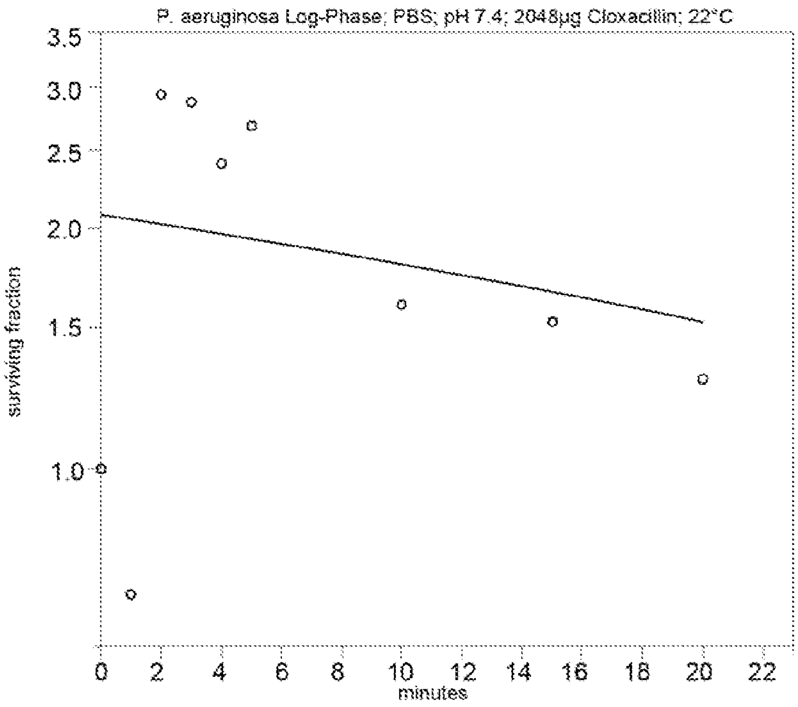
FIG. 24 illustrates the non-substantial killing effect of a pH 7.4 PBS solution having 2048 μg/ml cloxacillin at 22° C. on a logarithmic-phase *Pseudomonas aeruginosa* culture over a 20 minute period.
Figure 25:
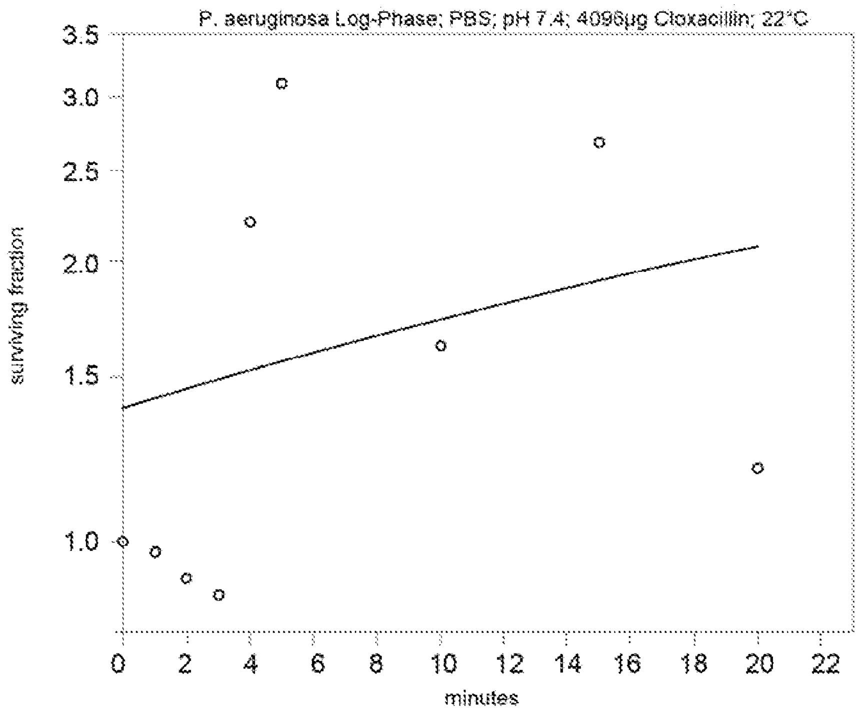
FIG. 25 illustrates the non-substantial killing effect of a pH 7.4 PBS solution having 4096 μg/ml cloxacillin at 22° C. on a logarithmic-phase *Pseudomonas aeruginosa* culture over a 20 minute period.
Figure 26:
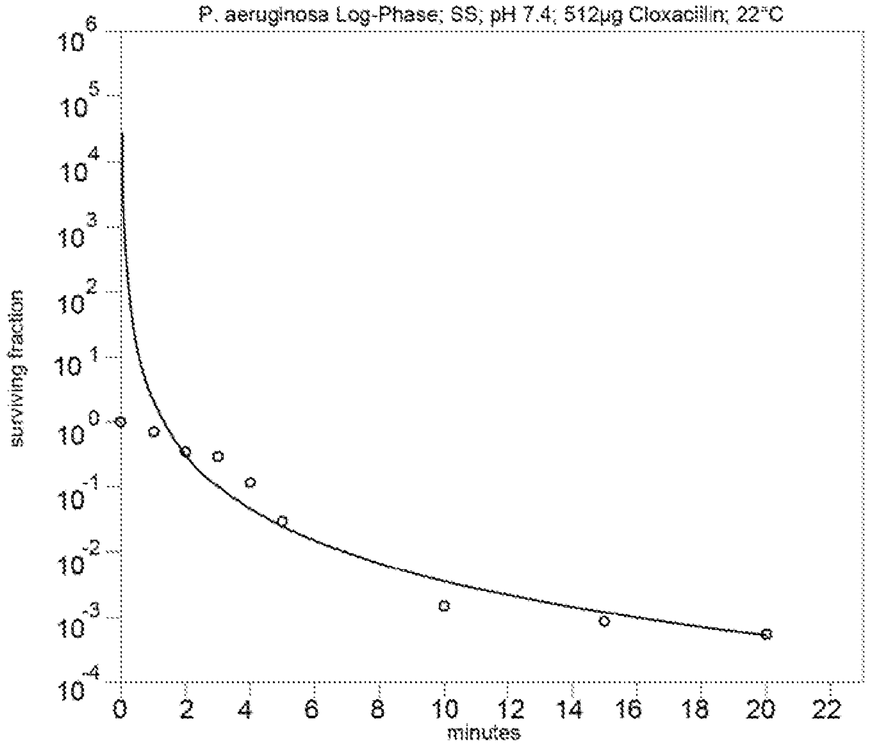
FIG. 26 illustrates the killing effect of a pH 7.4 SS having 512 μg/ml cloxacillin at 22° C. on a logarithmic-phase *Pseudomonas aeruginosa* culture over a 20 minute period.
Figure 27:
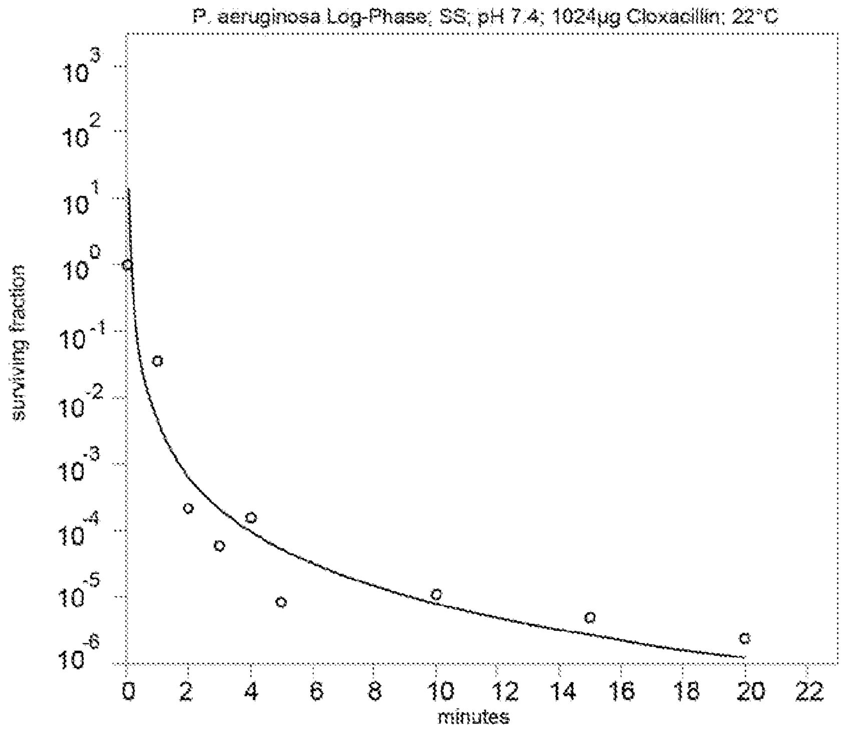
FIG. 27 illustrates the killing effect of a pH 7.4 SS having 1024 μg/ml cloxacillin at 22° C. on a logarithmic-phase *Pseudomonas aeruginosa* culture over a 20 minute period.
Figure 28:
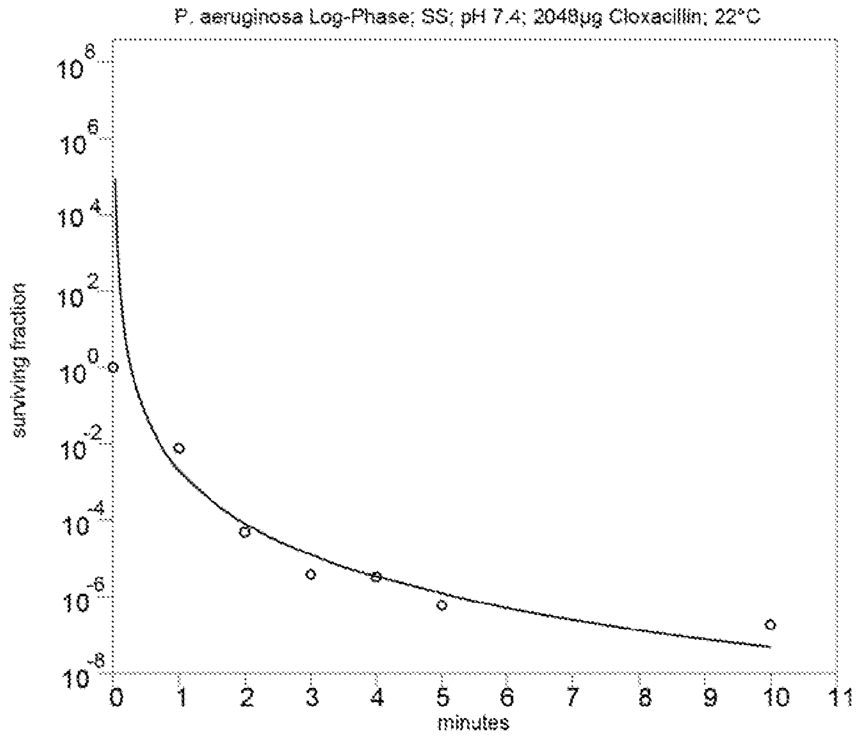
FIG. 28 illustrates the killing effect of a pH 7.4 SS having 2048 μg/ml cloxacillin at 22° C. on a logarithmic-phase *Pseudomonas aeruginosa* culture over a 10 minute period.
Figure 29:
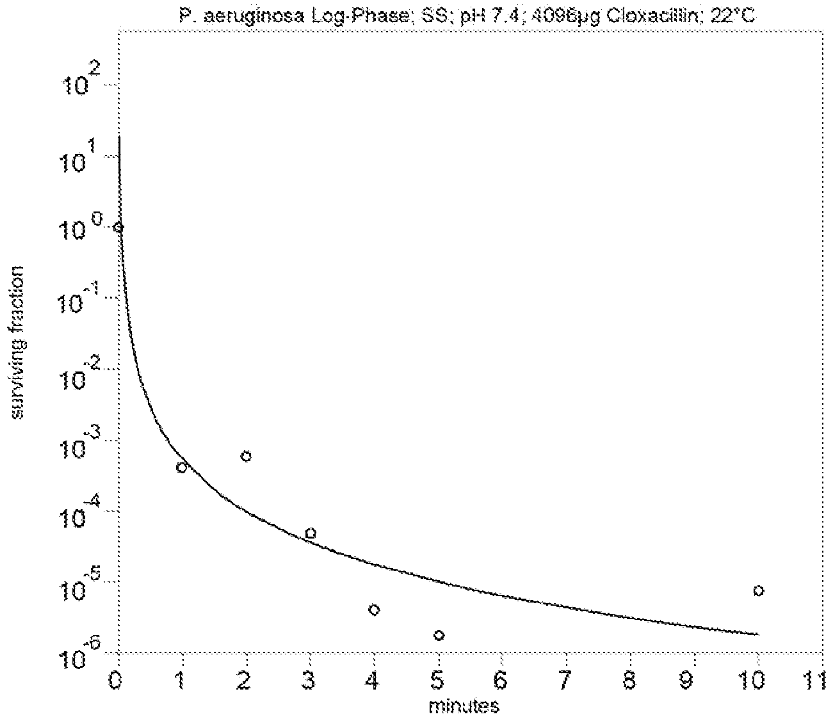
FIG. 29 illustrates the killing effect of a pH 7.4 SS having 4096 μg/ml cloxacillin at 22° C. on a logarithmic-phase *Pseudomonas aeruginosa* culture over a 10 minute period.
Figure 30:
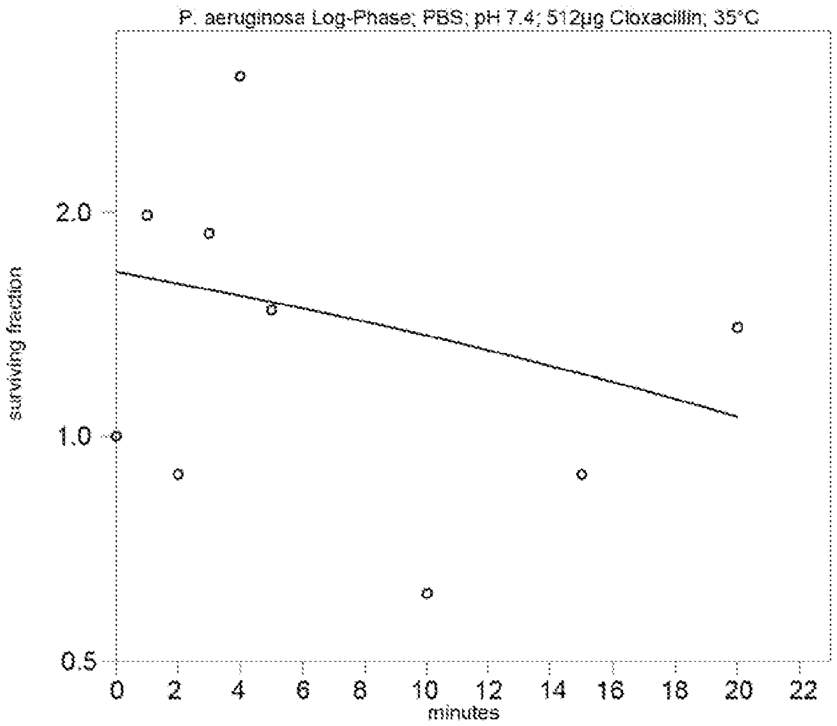
FIG. 30 illustrates the non-substantial killing effect of a pH 7.4 PBS solution having 512 μg/ml cloxacillin at 35° C. on a logarithmic-phase *Pseudomonas aeruginosa* culture over a 20 minute period.
Figure 31:
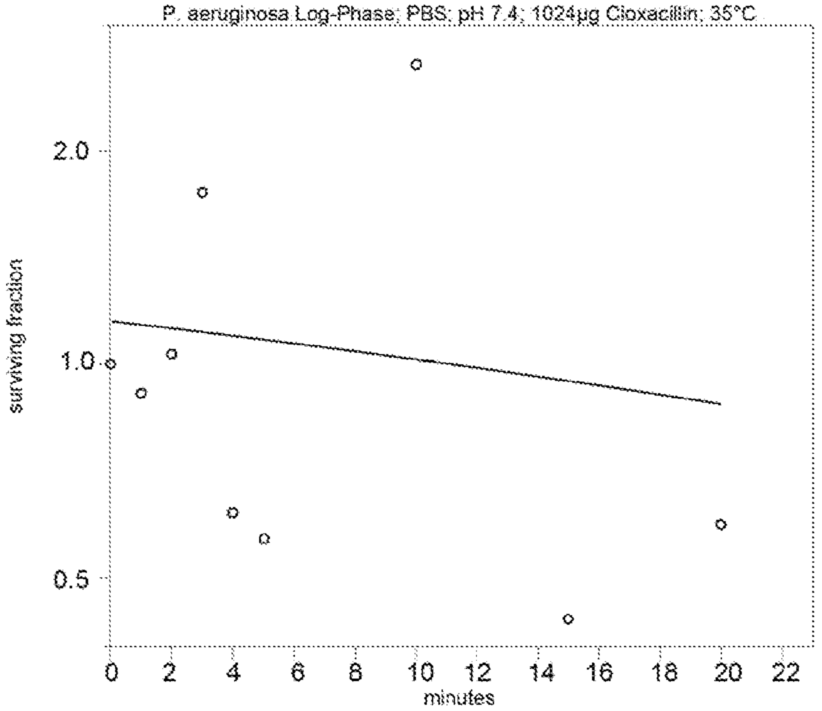
FIG. 31 illustrates the non-substantial killing effect of a pH 7.4 PBS solution having 1024 μg/ml cloxacillin at 35° C. on a logarithmic-phase *Pseudomonas aeruginosa* culture over a 20 minute period.
Figure 32:
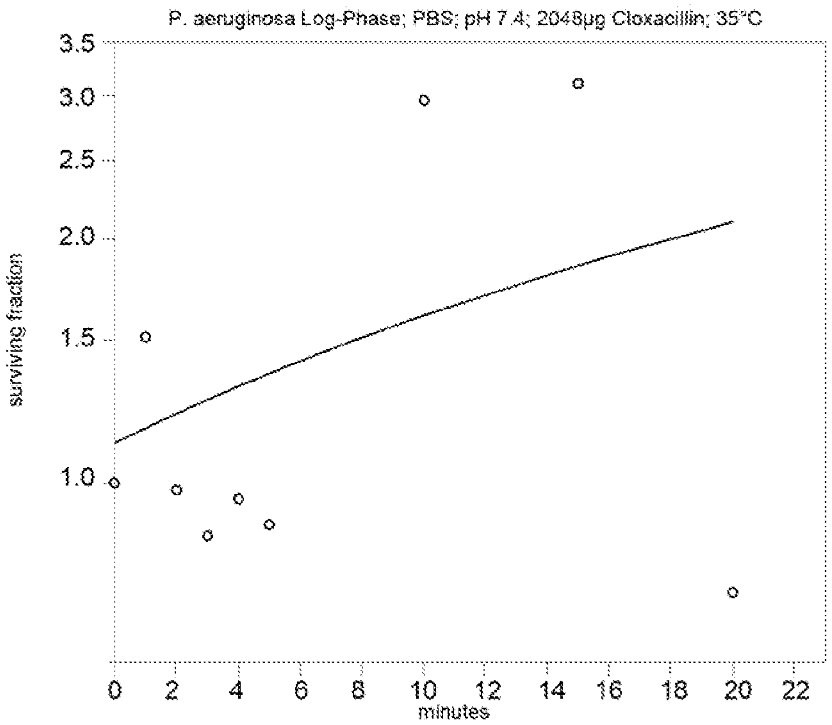
FIG. 32 illustrates the non-substantial killing effect of a pH 7.4 PBS solution having 2048 μg/ml cloxacillin at 35° C. on a logarithmic-phase *Pseudomonas aeruginosa* culture over a 20 minute period.
Figure 33:
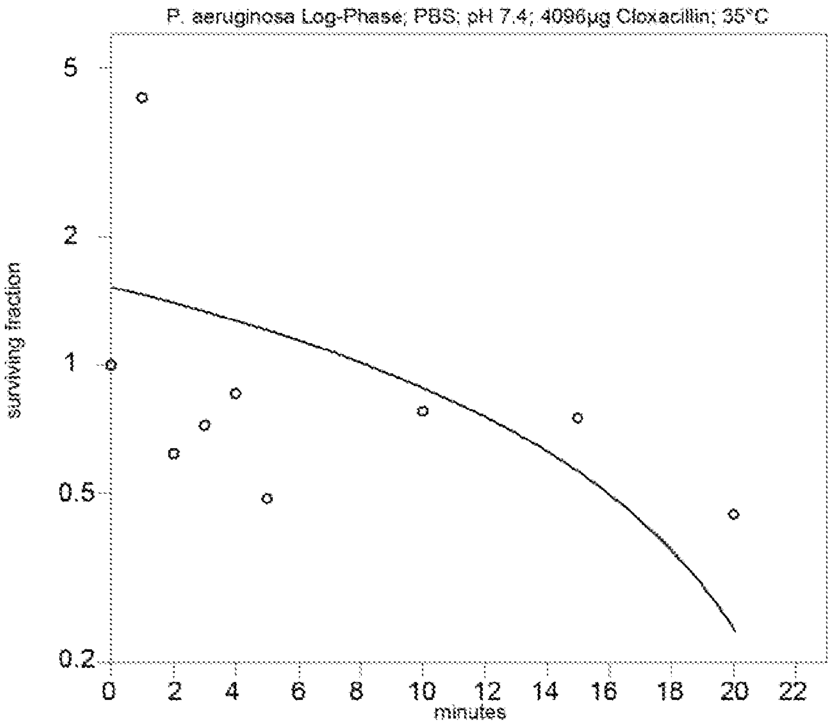
FIG. 33 illustrates the non-substantial killing effect of a pH 7.4 PBS solution having 4096 μg/ml cloxacillin at 35° C. on a logarithmic-phase *Pseudomonas aeruginosa* culture over a 20 minute period.
Figure 34:
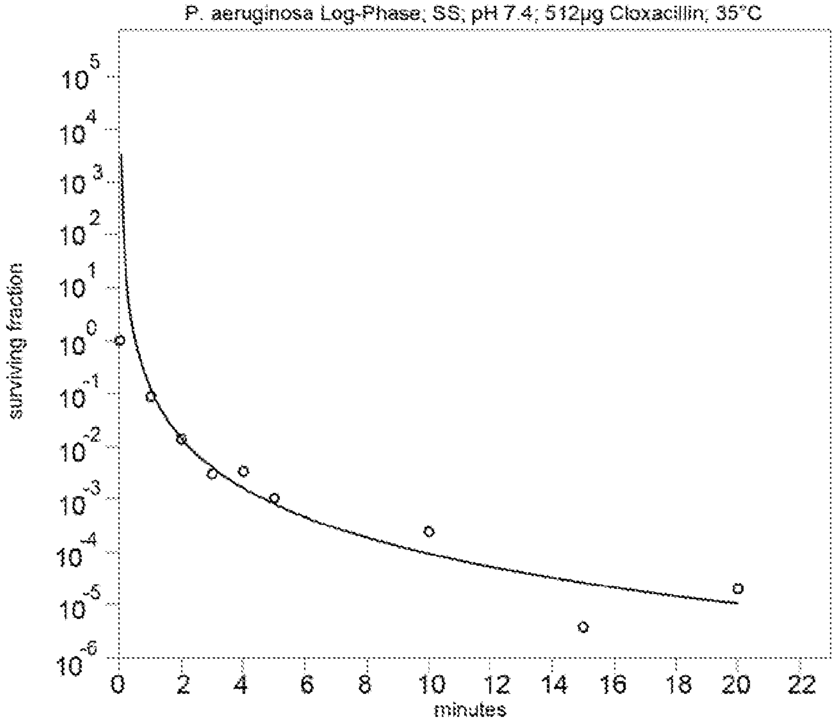
FIG. 34 illustrates the killing effect of a pH 7.4 SS having 512 μg/ml cloxacillin at 35° C. on a logarithmic-phase *Pseudomonas aeruginosa* culture over a 20 minute period.
Figure 35:
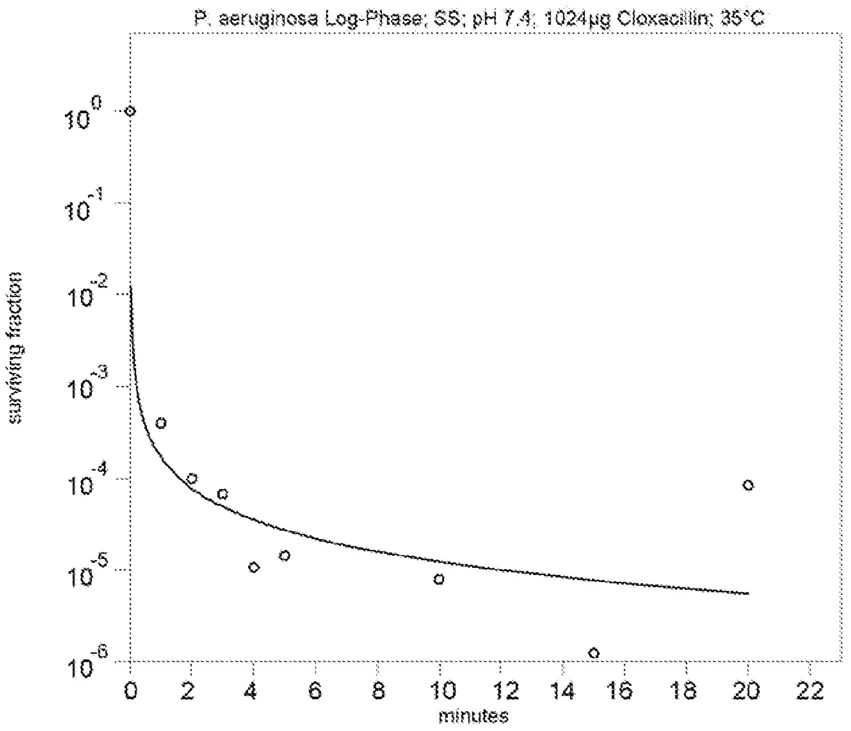
FIG. 35 illustrates the killing effect of a pH 7.4 SS having 1024 μg/ml cloxacillin at 35° C. on a logarithmic-phase *Pseudomonas aeruginosa* culture over a 20 minute period.
Figure 36:
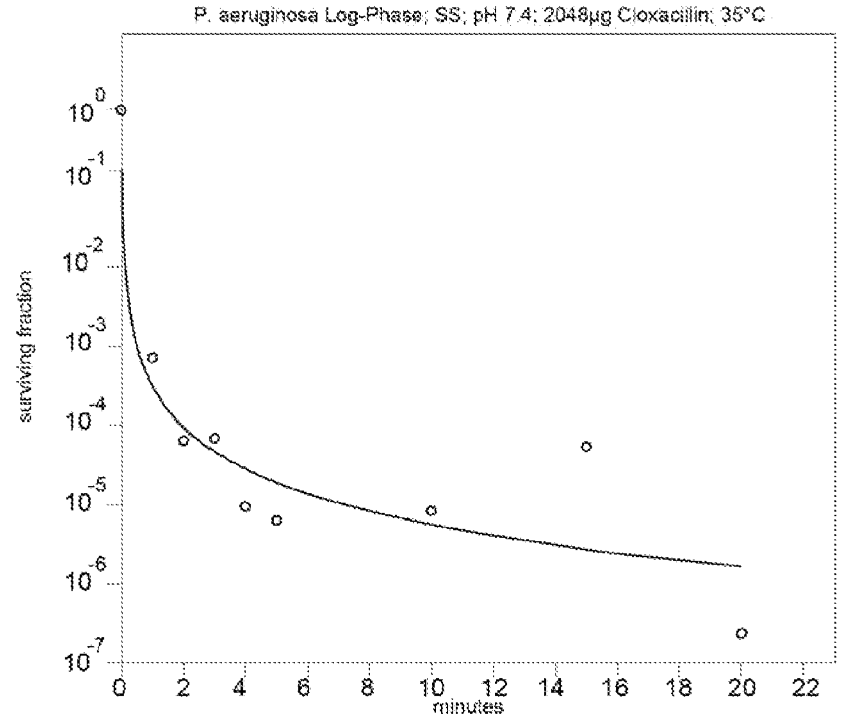
FIG. 36 illustrates the killing effect of a pH 7.4 SS having 2048 μg/ml cloxacillin at 35° C. on a logarithmic-phase *Pseudomonas aeruginosa* culture over a 20 minute period.
Figure 37:
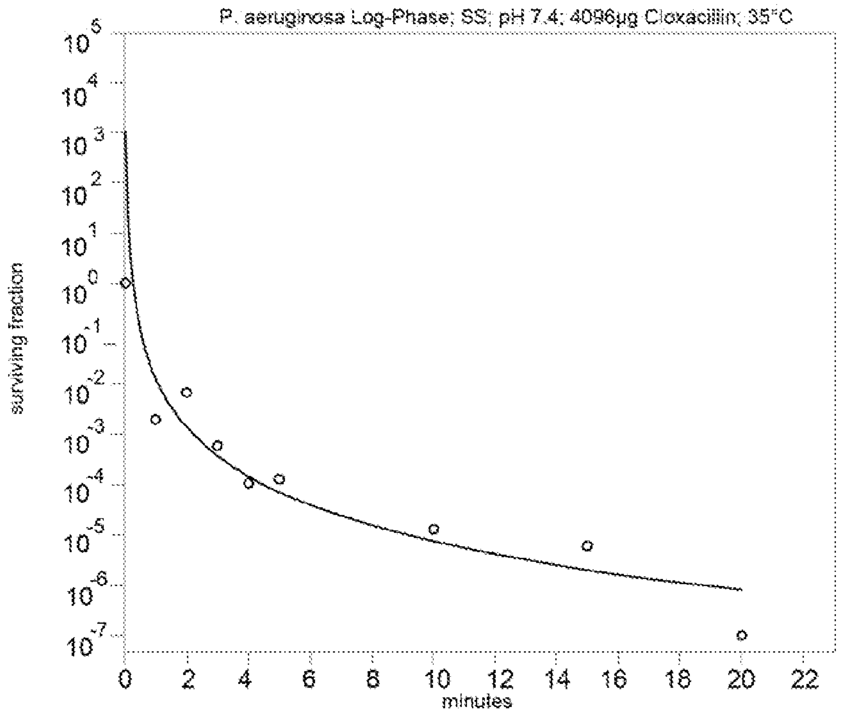
FIG. 37 illustrates the killing effect of a pH 7.4 SS having 4096 μg/ml cloxacillin at 35° C. on a logarithmic-phase *Pseudomonas aeruginosa* culture over a 20 minute period.
Figure 38:
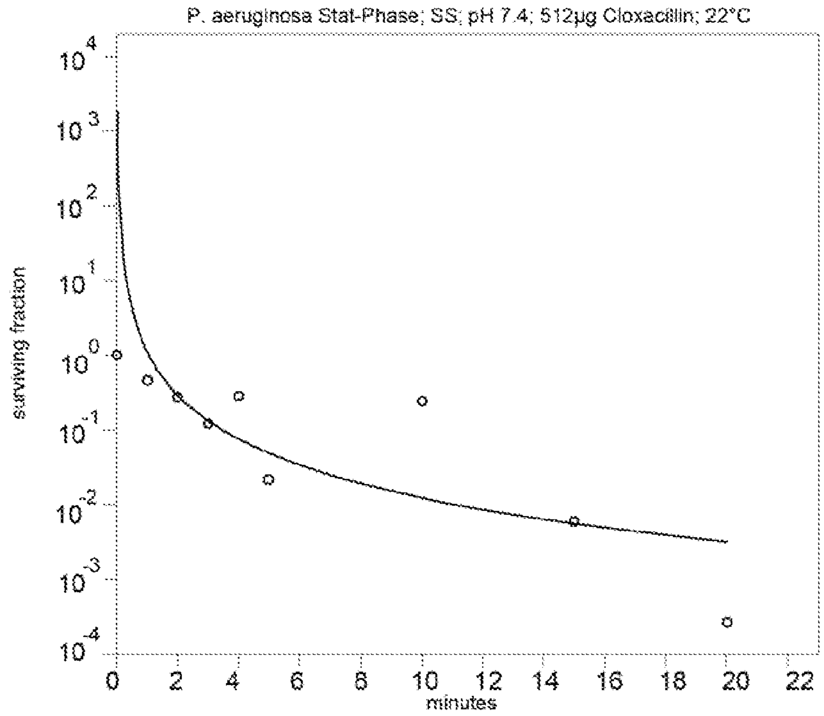
FIG. 38 illustrates the killing effect of a pH 7.4 SS having 512 μg/ml cloxacillin at 22° C. on a stationary-phase *Pseudomonas aeruginosa* culture over a 20 minute period.
Figure 39:
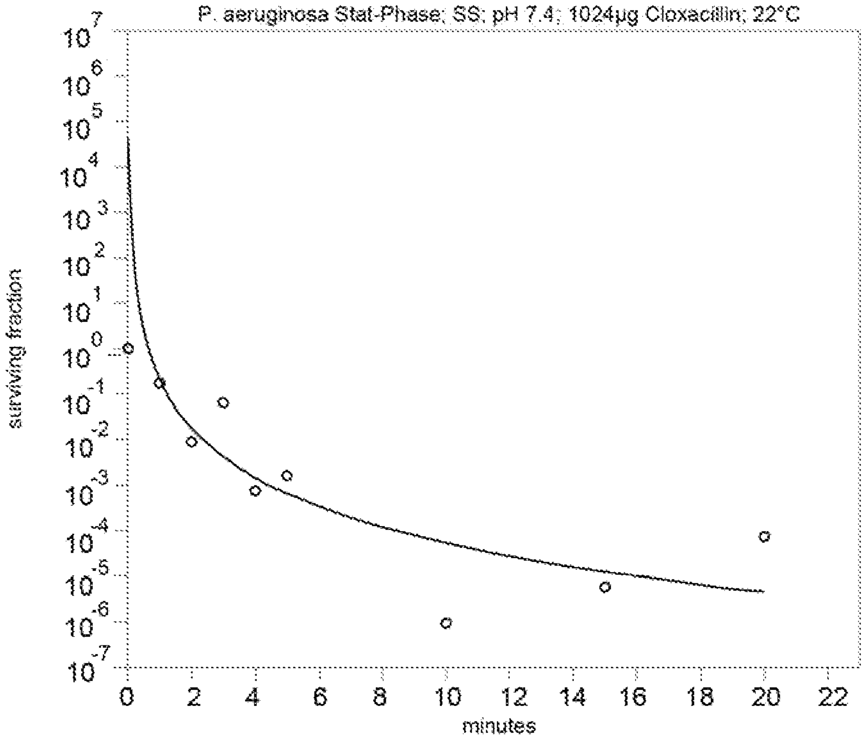
FIG. 39 illustrates the killing effect of a pH 7.4 SS having 1024 μg/ml cloxacillin at 22° C. on a stationary-phase *Pseudomonas aeruginosa* culture over a 20 minute period.
Figure 40:
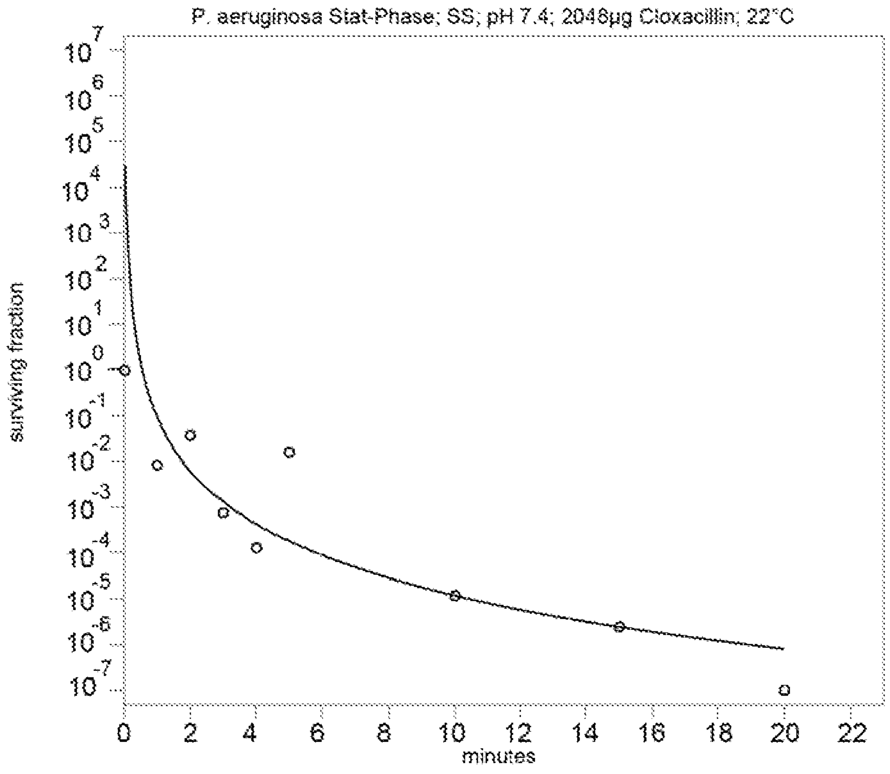
FIG. 40 illustrates the killing effect of a pH 7.4 SS having 2048 μg/ml cloxacillin at 22° C. on a stationary-phase *Pseudomonas aeruginosa* culture over a 20 minute period.
Figure 41:
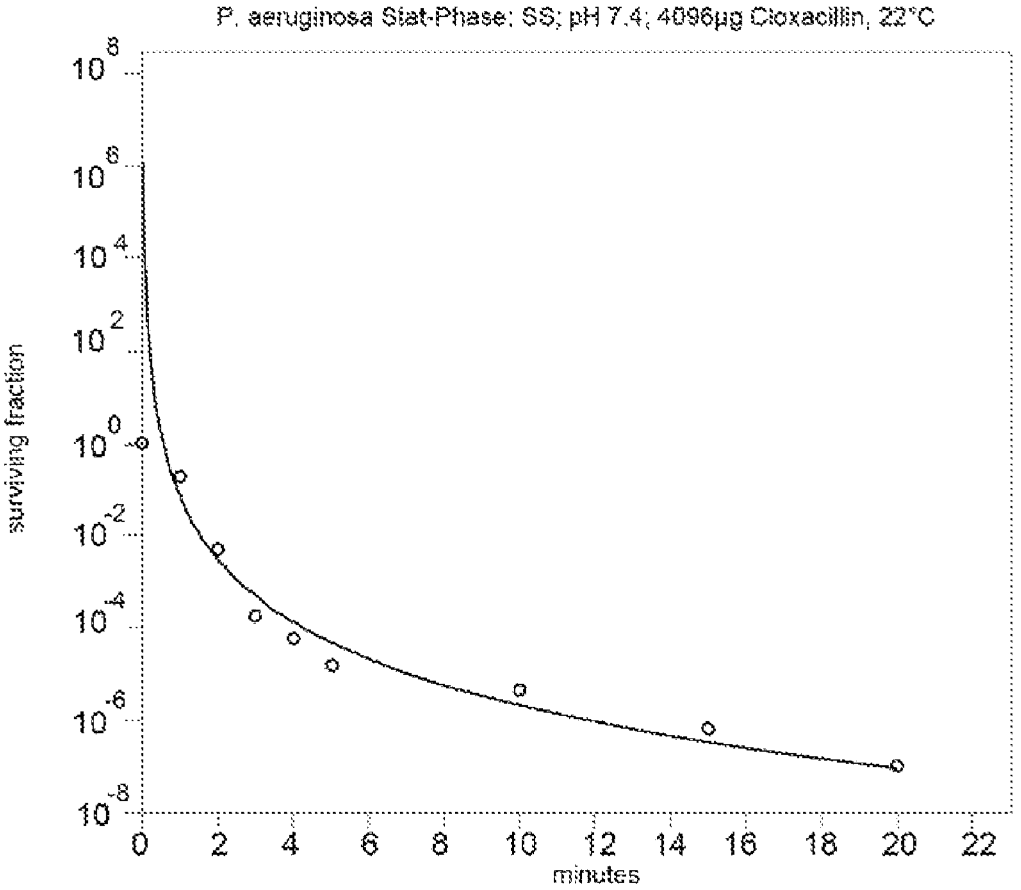
FIG. 41 illustrates the killing effect of a pH 7.4 SS having 4096 μg/ml cloxacillin at 22° C. on a stationary-phase *Pseudomonas aeruginosa* culture over a 20 minute period.

FIGS. 18 through 21 show the results of the control experiments. For the control experiments, logarithmic-phase *Pseudomonas aeruginosa* cells were treated in PBS (FIG. 18) or SS (FIG. 19), and stationary-phase *Pseudomonas aeruginosa* were treated in PBS (FIG. 20) or SS (FIG. 21). All experiments were conducted at both 22° C. and 35° C. for 60 minutes. No substantial killing was observed for any of these controls.

FIGS. 22 through 25 illustrate the non-substantial killing logarithmic-phase *Pseudomonas aeruginosa* using a PBS solution with cloxacillin concentrations ranging from 512 μg/ml to 4096 μg/ml at pH 7.4. The experiments were conducted at 22° C. for 20 minutes.

FIGS. 26 through 29 illustrate the efficiency of killing logarithmic-phase *Pseudomonas aeruginosa* using SS with cloxacillin concentrations ranging from 512 μg/ml to 4096 μg/ml at pH 7.4. For cloxacillin concentrations of 2048 μg/ml and 4096 μg/ml, the experiments were conducted at 22° C. for 20 minutes. For cloxacillin concentrations of 512 μg/ml and 1024 μg/ml, the experiments were conducted at 22° C. for 10 minutes. At all concentrations of cloxacillin, the SS, but not the PBS solution, was substantially efficient in killing *Pseudomonas aeruginosa.*

FIGS. 30 through 33 illustrate the non-substantial killing of logarithmic-phase *Pseudomonas aeruginosa* using a PBS solution with cloxacillin concentrations ranging from 512 μg/ml to 4096 μg/ml at pH 7.4. The experiments were conducted at 35° C. for 20 minutes.

FIGS. 34 through 37 illustrate the substantial killing of logarithmic-phase *Pseudomonas aeruginosa* using the SS with cloxacillin concentrations ranging from 512 μg/ml to 4096 μg/ml at pH 7.4. The experiments were conducted at 35° C. for 20 minutes.

FIGS. 38 through 41 illustrate the substantial killing of stationary-phase *Pseudomonas aeruginosa* using SS with cloxacillin concentrations ranging from 512 μg/ml to 4096 μg/ml at pH 7.4. The experiments were conducted at 22° C. for 20 minutes.

Killing is more efficient for cells exposed to higher concentrations of cloxacillin. In the embodiments shown, the highest concentration of cloxacillin tested was 4096 μg/ml; however, it is not necessarily the maximum effective or tolerated concentration. The concentration of cloxacillin or other drug may be varied depending on the contact effect required for topical applications in any given situation. That is, the preferred concentration should be determined for each specific application.

The use of various concentrations of compounds from the Hofmeister series can affect macromolecular hydration and protein denaturation, which may expose novel penicillin-binding amino acid motifs of PBPs and other non-specific proteins. In addition, high salt concentrations inactivate efflux transporters and porins. As a result, both penicillin-resistant Gram-positive and Gram-negative pathogenic bacteria may be created as penicillin-sensitive by physico-chemical denaturation induced by exposure to the embodied SS and related salt solutions when containing penicillin. It is expected that under these specific conditions, universal creation of protein target sensitivity to penicillin results from such physico-chemical treatment, that is, a field effect of covalent binding of proteins to penicillin is established during the physico-chemical treatment by SS in the presence of penicillin. This field effect, whereby any affected bacterial proteins may be modified to enhance penicillin-binding, promotes direct killing and allows, for the first time, the potential application of penicillin to control static cells, including stationary-phase cells, as well as actively growing cultures of bacteria. Penicillin dissolves well in the SS described and may be used for treatment in the form of a topical application.

Cloxacillin at relatively high concentration in the SS substantially kills static logarithmic-phase and static stationary-phase penicillin-resistant MRSA and *Pseudomonas aeruginosa* cells rapidly upon exposure at room temperature, and the degree of killing is advanced using variables of pH and temperature. This substantial killing of static penicillin-resistant bacteria at room temperature is notable in that the killing effectiveness is established in both logarithmic-phase and stationary-phase Gram-positive and Gram-negative bacteria.

The embodiment of discovery and application described for physico-chemically induced alteration of in situ target proteins producing creation of sensitivity to otherwise ineffective penicillin is of great value in regard to both concepts and applications for continuing efforts to remedy clinical penicillin-resistance, and by extension a spectrum of related drug-resistance.

The fact that penicillin-resistant static bacteria, both Gram-positive and Gram-negative, are killed directly using a topically innocuous solution immediately applies to topical treatments such as those involved in pre-surgical fields so that contaminating penicillin-resistant bacteria will be purged prior to surgical procedures, thus eliminating subsequent parenteral infections that currently plague clinical invasive procedures. Topical applications include, but are not limited to skin colonization, suppurating infections, infections of the eye, nares, throat and mouth, wounds, burns, encysted infections, cellulitis, fulminating fasciitis, and also bacterial infection upon internal structures, such as the vagina, urinary tract and bladder, peritoneal cavity, large intestine, lung and trachea, stomach, etc., all of which are accessible to instillation procedures.

In addition, bacterial infections are a complicating factor in space travel. Injuries and radiation burns do not heal as well in space, resulting in nagging injuries which may affect an astronaut's performance. The present invention provides a new ability to fight infections in space.

Bacterial infections are also a major factor for the Department of Defense, especially during war times. Often, injuries that occur in the field become infected with the subject bacteria and are barely treatable. Use of the present invention provides an improved method for wound and burn healing. Likewise, the Department of Homeland Security is concerned about infections that result from radiation burns occurring at dirty bomb sites. The use of the present invention would provide a new and simple way of dealing with that issue.

The present invention operates in physico-chemical mode, which exposes normally inaccessible target motifs for covalent binding of penicillin, thus demonstrating for the first time a mechanism of action for penicillin that is outside the dogma of biochemical action of penicillin upon only transpepidases in actively growing bacterial cells.

The present embodiment claims rearrangement of macromolecules using compounds from the Hofmeister series, thereby yielding new target motifs accessible by drugs and/or anti-toxins carried in the SS, which may be applied topically to manage resistant or problematic organisms and/or macromolecules. The scope of this discovery includes topical applications for treatment of bacteria; viruses; molds and yeasts; topical parasites, such as ring-worm, ticks, and cutaneous and mucocutaneous Leishmania; and pathological macromolecules, such as bacterial exotoxins and endotoxins, snake and spider venoms, super-antigens, and prions. "Topical application" includes application not only to skin, but also to cystic and suppurating infections, wounds, burns, nares, throat, mouth, as well as all instillations such as to the urinary tract and bladder, vagina, peritoneal cavity, large intestine, stomach, lung, and trachea. The mechanism of denaturation and rearrangement of macromolecules, and not only proteins, contributes to the disruption of pathologic processes by compounds of the Hofmeister series, opening new accessibility to molecular target motifs for effective management by drugs, such as penicillins, and anti-toxins, such as silver ions, carried in specifically optimized SS. Combinations of drugs and antitoxins may be applied in this regard. For example, in topical applications of the SS to fulminating fasciitis, a condition requiring rapid and multiple reversals of currently resistant pathologic processes, penicillin may be included to kill bacteria and silver ions may be included to inactivate super-antigens.

The present embodiment claims management of water activity and structure associated with macromolecules in bacterial pathogens by use of compounds of the Hofmeister series, and examines the substantial killing effects due to new target motifs that react with penicillin in planktonic bacteria during exposures to the SS. Topical clinical applications of the SS carrying drugs and/or anti-toxins will, however, encounter sessile, as well as planktonic bacteria, the principal additional barrier to accessibility by drugs and/or anti-toxins then being the biofilm of polysaccharides, mucopeptides, etc. secreted by and covering the sessile bacteria. It is expected that dehydration and denaturation by humectant-like and other compounds from the Hofmeister series in the SS will permeabilize this highly hydrated biofilm to drugs and/or anti-toxins, as well as expose new target motifs and inactivate outer membrane-associated accessibility barriers as shown in the embodiment herein.

What is claimed is:

1. A pharmaceutical composition comprising: a potassium cation; an ammonium cation; a phosphate anion; a sulfate anion; an acetate anion; and a penicillin; wherein said potassium cation, said ammonium cation, said phosphate anion, said sulfate anion, said acetate anion, and said penicillin are in a solution having a pH ranging from 3.5 to 10; wherein said solution has a temperature ranging from 0° C. to 43° C.; wherein each of said potassium cation, said ammonium cation, said phosphate anion, said sulfate anion, and said acetate anion has a molar concentration ranging from 0.01 M to 4.0 M and are of a concentration which induces alteration of in situ target proteins to establish sensitivity of bacteria to otherwise ineffective penicillins.

2. The pharmaceutical composition of claim 1 wherein said potassium cation has a molar concentration of 2.6 M.

3. The pharmaceutical composition of claim 1 wherein said ammonium cation has a molar concentration of 3.7 M.

4. The pharmaceutical composition of claim 1 wherein said phosphate anion has a molar concentration of 3.1 M.

5. The pharmaceutical composition of claim 1 wherein said sulfate anion has a molar concentration of 0.4 M.

6. The pharmaceutical composition of claim 1 wherein said acetate anion has a molar concentration of 0.2 M.

7. The pharmaceutical composition of claim 1 which further includes free ammonia.

8. The pharmaceutical composition of claim 1 wherein said solution is at 22° C.

9. The pharmaceutical composition of claim 1 wherein said solution is at 37° C.

10. The pharmaceutical composition solution of claim 1 wherein said bacteria are Gram-positive.

11. The pharmaceutical composition solution of claim 1 wherein said bacteria are methicillin-resistant *Staphylococcus aureus* (MRSA).

12. The pharmaceutical composition solution of claim 1 wherein said bacteria are Gram-negative.

13. The pharmaceutical composition solution of claim 1 wherein said bacteria are *Pseudomonas aeruginosa.*

14. The pharmaceutical composition solution of claim 1 wherein said penicillin is semi-synthetic penicillin.

15. The pharmaceutical composition solution of claim 1 wherein said penicillin is cloxacillin.

16. The pharmaceutical composition solution of claim 1 wherein said penicillin concentration is between 512 μg/mL and 4096 μg/mL.

17. A method of making a pharmaceutical composition comprising the steps of:

providing a potassium cation, an ammonium cation, a phosphate anion, a sulfate anion, an acetate anion, a penicillin; and ammonium hydroxide; placing said potassium cation, said ammonium cation, said phosphate anion, said sulfate anion, said acetate anion into an aqueous solution in a proportional concentration which induces alteration of in situ target proteins to establish sensitivity of bacteria to otherwise ineffective penicillins; adding said penicillin to said solution; and using said ammonium hydroxide to bring said solution to a desired pH.

18. The method of claim 17 which further comprises the step of bringing said solution to a desired temperature.

19. The method of claim 18 wherein said desired temperature is 22° C.

20. The method of claim 18 wherein the desired temperature is 37° C.

21. The method of claim 17 wherein said composition is adapted for administration by topical application.

22. The method of claim 17 wherein said composition is adapted for administration by oral ingestion.

23. The method of claim 17 wherein said composition is adapted for administration by inhalation.

24. The method of claim 17 wherein said composition is adapted for administration by instillation.

25. The method of claim 17 wherein said bacteria are in a stationary growth phase.

26. The method of claim 17 wherein said bacteria are in a logarithmic growth phase.

27. The method of claim 17 wherein said bacteria are methicillin-resistant *Staphylococcus aureus* (MRSA).

28. The method of claim 17 wherein said bacteria are *Pseudomonas aeruginosa.*

29. The method of claim 17 wherein said penicillin is semi-synthetic penicillin.

30. The method of claim 29 wherein the penicillin is cloxacillin.

31. The method of claim 17 wherein said penicillin concentration is between 512 μg/ml and 4096 μg/ml.

32. The method of claim 17 wherein said potassium cation has a molar concentration of 2.6 M.

33. The method of claim 17 wherein said ammonium cation has a molar concentration of 3.7 M.

34. The method of claim 17 wherein said phosphate anion has a molar concentration of 3.1 M.

35. The method of claim 17 wherein said sulfate anion has a molar concentration of 0.4 M.

36. The method of claim 17 wherein said acetate anion has a molar concentration of 0.2 M.

* * * * *